United States Patent [19]

Iyer et al.

[11] Patent Number: 5,939,050
[45] Date of Patent: Aug. 17, 1999

[54] ANTIMICROBIAL COMPOSITIONS

[75] Inventors: Lokanathan M. Iyer, Edmonds; James R. Scott; Douglas F. Whitfield, both of Bothell, all of Wash.

[73] Assignee: Optiva Corp., Bellevue, Wash.

[21] Appl. No.: 08/832,821

[22] Filed: Apr. 4, 1997

[51] Int. Cl.⁶ .............................. A61K 7/16; A61K 7/26
[52] U.S. Cl. ............... 424/49; 424/54; 424/58; 424/405; 514/900; 514/901; 514/902
[58] Field of Search ................. 424/49, 54, 58, 424/405; 514/900, 901, 902

[56] References Cited

U.S. PATENT DOCUMENTS

| | | | |
|---|---|---|---|
| 3,787,566 | 1/1974 | Gauvreau | 424/45 |
| 3,940,476 | 2/1976 | Haas | 424/49 |
| 4,022,880 | 5/1977 | Vinson et al. | 424/49 |
| 4,145,412 | 3/1979 | Ladanyi | 424/58 |
| 4,406,881 | 9/1983 | Ladanyi | 424/49 |
| 4,545,979 | 10/1985 | Ambike et al. | 424/52 |
| 4,550,018 | 10/1985 | Ambike et al. | 424/52 |
| 4,599,228 | 7/1986 | Ladanyi | 424/52 |
| 4,839,158 | 6/1989 | Michaels | 424/54 |
| 4,894,220 | 1/1990 | Nabi et al. | 424/52 |
| 4,913,895 | 4/1990 | Miyake et al. | 424/57 |
| 4,933,182 | 6/1990 | Higashi et al. | 424/435 |
| 4,961,924 | 10/1990 | Suhonen | 424/52 |
| 4,966,754 | 10/1990 | Purohit et al. | 424/195.1 |
| 4,992,259 | 2/1991 | Schiraldi et al. | 424/49 |
| 4,999,184 | 3/1991 | Parran, Jr. et al. | 424/52 |
| 5,004,597 | 4/1991 | Majeti et al. | 424/52 |
| 5,009,884 | 4/1991 | Suhonen | 424/52 |
| 5,009,898 | 4/1991 | Sakuma et al. | 424/618 |
| 5,017,363 | 5/1991 | Suhonen | 424/52 |
| 5,094,843 | 3/1992 | Mazzanobile et al. | 424/52 |
| 5,135,747 | 8/1992 | Faryniarz et al. | 424/401 |
| 5,145,666 | 9/1992 | Lukacovic et al. | 424/52 |
| 5,190,944 | 3/1993 | Hsu | 514/244 |
| 5,190,979 | 3/1993 | Herman | 514/762 |
| 5,213,790 | 5/1993 | Lukacovic et al. | 424/52 |
| 5,256,402 | 10/1993 | Prencipe et al. | 424/53 |
| 5,268,174 | 12/1993 | Sakuma et al. | 424/195.1 |
| 5,281,410 | 1/1994 | Lukacovic et al. | 424/52 |
| 5,281,411 | 1/1994 | Majeti et al. | 424/52 |
| 5,298,238 | 3/1994 | Hussein et al. | 424/49 |
| 5,316,760 | 5/1994 | Voerman | 424/58 |
| 5,338,537 | 8/1994 | White, Jr. et al. | 424/52 |
| 5,374,418 | 12/1994 | Oshino et al. | 424/54 |
| 5,376,374 | 12/1994 | Zelaya | 424/195.1 |
| 5,378,465 | 1/1995 | Zeines | 424/195.1 |
| 5,409,692 | 4/1995 | Nakahara et al. | 424/49 |
| 5,453,276 | 9/1995 | Nakatsu et al. | 424/405 |
| 5,468,489 | 11/1995 | Sakuma et al. | 424/49 |
| 5,472,684 | 12/1995 | Nabi et al. | 424/49 |
| 5,658,584 | 8/1997 | Yamaguchi | 424/405 |

FOREIGN PATENT DOCUMENTS

| | | |
|---|---|---|
| 0 805 198 | 11/1997 | European Pat. Off. . |
| 2 377 195 | 8/1978 | France . |
| 2 743 722 | 7/1997 | France . |
| 46-28430 | 8/1971 | Japan . |
| 58-140014 | 8/1983 | Japan . |
| 59-175410 | 10/1984 | Japan . |
| 7-89819 | 4/1995 | Japan . |

OTHER PUBLICATIONS

Translation of 59–175410 Jan. 27, 1995, Japan.
Translation of 58–140014 Aug. 19, 1983, Japan.
Translation of 46–28430 Aug. 18, 1971, Japan.
Translation of 7–89819 Aug. 18, 1971, Japan.
Translation of 2 377 195 Aug. 11, 1978, France.
Translation of 2 743 722 Jul. 25, 1997, France.
Derwent Abstract No. 007182410. Jul. 1987.
Kabara, J.J., "Aroma Preservatives: Essential Oils and Fragrances as Antimicrobial Agents," *Cosmetic and Drug Preservation: Principles and Practice*, pp. 237–273, 1984.
Yokata, Masaharu et al.; "Antimicrobial effect of aromatic natural compound, cheifly against Staphyloccus aureus"; *ASSN*0019–1604; Igaku to Seibutsugaku; 128(3):105–10;;1994.
Translation of Yokota, Masaharu et al.; "Antimicrobial effect of aromatic natural compound, cheifly against Staphylococcus aureus"; *ASSN*:0019–1604; Igaku to Seibutsugaku;128(3):105–10; 1994.
Kedzia, B. et al.; "Composition and antimicrobial characteristics of Melissa oil and its components"; *Herba Polonica*40(1–2), 5–11; 1994.
Translation ofKedzia, B. et al.; "Composition and antimicrobial characteristics of Melissa oil and its components", *Herba Polonica*; 40(1–2), 5–11;1994.
Azuma, Masahiro, Kubota, Minoru; "Aromatic bactericides preparation from hinoki oil and white cedar oil"; CA:123:3404; Apr. 4, 1995.
Kanebo Foods, Ltd.; "Anticaries agents"; CA:102:31949; Oct. 4, 1984.
Yokota, Masaharu et al.; "Antimicrobial effect of aromatic natural compound, chiefly against *Staphylococcus aureus*"; CA:121–53735; 1994.
Doi, Tadahiro et al.; "Chloramphenicol suspension"; CA:75:133025; Aug. 18, 1971.
S.S. Pharmaceutical Co., Ltd.; "Transparent liquid pharmaceuticals"; CA:99:181502; Aug. 19, 1983.
Adames, Marlene et al.; "Study of the essential oil of Eucalyptus citriodora Bailey"; CA:101:59975; ISSN:0034–7418; Inst. Roslin Przetworow Zielarskich; 4(1):95–113; 1983.
Kedzia, B. et al.; "Composition and antimicrobial characteristics of Melissa oil and its components"; CA:121–263407; ISSN: 0018–0599; 40(1–2), 5–11; 1994.
Megallia, S.E. et al.; "A Study of Antimicrobial Action of Some Essentia Oil Constituents"; *Herba Pol.*; 26(3):181–186; 1980.
Morris, J.A. et al.; "Antimicrobial Activity of Aroma Chemicals and Essential Oils"; *J. Am. Oil Chem. Soc.*; 56(5):595–603; 1979.

*Primary Examiner*—S. Mark Clardy
*Attorney, Agent, or Firm*—Christensen O'Connor Johnson & Kindness PLLC

[57] ABSTRACT

Antimicrobial compositions comprising at least two antimicrobial agents exhibit reduced MIC values relative to the MIC for the agents making up the combination when measured alone. The compositions are useful as therapeutic agents such as in oral hygiene products.

24 Claims, 1 Drawing Sheet

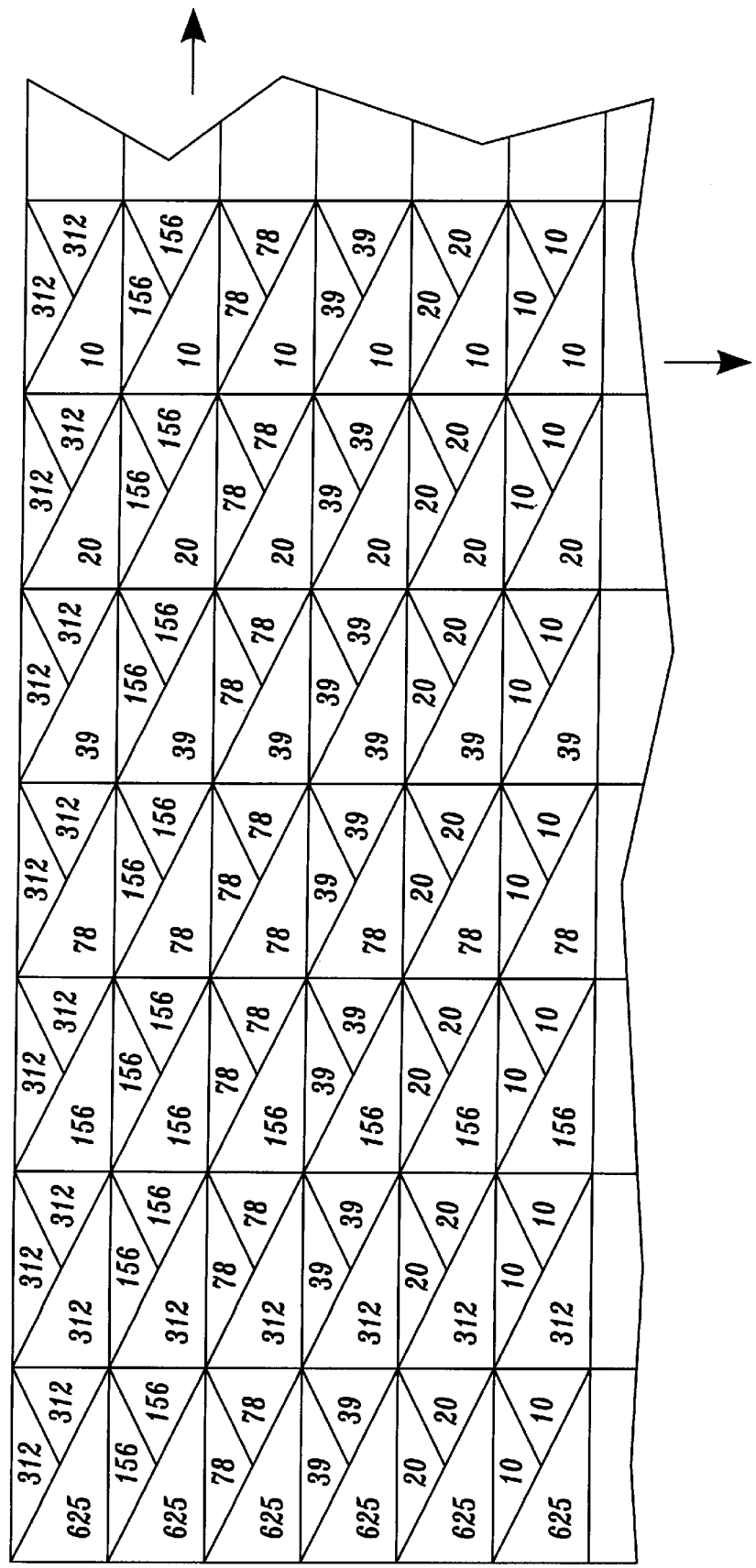

ANTIMICROBIAL COMPOSITIONS

FIELD OF THE INVENTION

The present invention relates to antimicrobial compositions, products incorporating such antimicrobial compositions, and applications for antimicrobial compositions.

BACKGROUND OF THE INVENTION

Periodontal disease and dental caries are of major public health and economic interest worldwide. It is now widely recognized that both of these oral diseases are caused by bacteria which grow in masses on the teeth and in the gingival area. A commonly used descriptive term for these bacterial masses is "dental plaque". In the case of periodontal disease, Schluger et al. (Schluger, Yuodelis, Page & Johnson, *Periodontal Diseases*, second edition, pp. 153–262, Lea & Febiger, 1990) report that dental plaque bacteria, growing in the area where the teeth and gingival tissues meet, cause an inflammation of the gingiva called "gingivitis". This is characterized by swollen, edematous gingiva ("gums") which are reddened and bleed easily. If plaque removal is inadequate, gingivitis may progress to "periodontitis" or periodontal disease in many individuals. Periodontitis generally is a characterized by a chronic inflammation of the tissues around the teeth, which leads to a resorption of supporting bone. Periodontal disease is the leading cause of tooth loss among adults. Dental caries (cavities) are also caused by bacteria, with *Streptococcus mutans* being the principal etiologic agent (McGhee, Michalek & Cassell, *Dental Microbiology*, p. 279, Harper & Row, 1982).

The prevention of dental plaque or the removal thereof has long been the focus of development, with the ultimate goal of inhibiting both caries and periodontal diseases. While the formation of dental plaque can be inhibited to a certain extent by brushing the teeth at frequent intervals, brushing along is not sufficient to effectively prevent the formation of dental plaque or remove substantially all of the dental plaque that has formed on the teeth. Since brushing alone is often not sufficient to prevent dental caries or periodontal disease due to pathogenic plaque bacteria, chemical methods using anti-bacterials such as chlorhexidine, benzalkonium chloride, and cetylpyridinium chloride have been proposed.

The use of natural products for the treatment of teeth and gums is old in the art, having been practiced and documented since the mid-1880s. Since then, many patents have disclosed compositions of oral products containing natural product extracts.

It is known that hinokitiol, citral, geraniol, cocamidopropyl betaine, berberine, and juniper berries oil, individually exhibit antimicrobial properties against certain bacteria.

U.S. Pat. No. 3,940,476 describes a method for inhibiting the formation of dental plaque, which comprises topically applying to the teeth as an active ingredient an amount of either one or a combination of (a) allyl isothiocyanate, (b) uranine, (c) obtusastyrene, (d) citral, (e) citronellol, (f) nerol, or (g) geraniol.

U.S. Pat. No. 4,913,895 describes an oral composition including a linear polyphosphate or a cyclic polyphosphate and menthol, anethol, or mixtures thereof in an aqueous medium. The composition is reported to have antibacterial effects and prevent the development of calculus and periodontal diseases.

U.S. Pat. No. 4,966,754 describes that certain essential oils and combinations thereof possess antimicrobial properties against *Aspergillus niger*, *Candida albicans*, *Staphylococcus aureus*, and *Pseudomonas aeruginosa* and therefore are useful as preservatives in cosmetic compositions. A blend of 14 essential oils is described as providing desirable antimicrobial properties against the noted microorganisms. The described combination is disclosed as being suitable as a preservative for cosmetic compositions.

U.S. Pat. No. 4,999,184 describes oil compositions containing certain pyrophosphate salts which are reported to provide an anticalculus benefit.

U.S. Pat. No. 5,316,760 describes a mouthcare product that contains a combination of *Urtica dioica* extract and an extract of *Juniperus communis*. The combination of these extracts is described as leading to a synergistic reduction of both dental plaque and bleeding or inflammation of the gingiva. *Achillaea millefolium* extract is also described as being a suitable additive to the combination of the *Urtica dioica* and *Juniperus communis* extracts.

U.S. Pat. No. 5,472,684 describes a composition including thymol and eugenol, and optionally a sesquiterpene alcohol, such as farnesol, that reportedly has antiplaque and antigingivitis effects. Australian tea tree oil, sage oil, and eucalyptol are described as enhancing the antiplaque and antigingivitis activity of mouth rinses formulated from the disclosed compositions.

One property that characterizes the effectiveness of an antimicrobial agent as an antiplaque and anticalculus agent is the minimum inhibitory concentration, or MIC, of the agent. The MIC is the minimum concentration in micrograms per milliliter of an antimicrobial agent at which no bacterial growth is observed. At concentrations below the MIC, an antimicrobial agent is ineffective at killing or inhibiting the growth and reproduction of bacteria. At concentrations above the MIC, an antimicrobial agent is effective at killing or inhibiting the growth and reproduction of bacteria.

Typically, antimicrobial agents are introduced into the oral cavity at an initial concentration. Almost immediately, the initial concentration begins to decrease due to the dynamics of the oral cavity. Eventually, the concentration of the antimicrobial agent within the oral cavity will fall below the MIC. Thus, it has been a goal of those working to develop antiplaque and anticalculus formulations to use antimicrobial agents that have low MICs.

Chlorhexidine has a MIC of about one $\mu$g/ml and is the standard against which other antimicrobial agents are measured. While chlorhexidine has a desirable MIC, it also exhibits undesirable taste and has the undesirable side effect of staining teeth.

SUMMARY OF THE INVENTION

The present invention relates to the present discovery that the addition of one antimicrobial agent described below to another antimicrobial agent described below results in an unexpected and surprising reduction of the minimum inhibitory concentration (MIC) of at least one of the agents when determined in the combination, i.e., in the presence of the other agent. In other words, the MIC for agent A, when measured in the presence of agent B, is less than the MIC of agent A when measured alone, i.e., in the absence of agent B. Thus, when in combination with agent B, antimicrobial agent A is able to effectively inhibit or prevent bacterial growth at concentrations lower than the MIC for agent A measured alone. When the combination of agent A and agent B results in the MIC of agent B being reduced to a value lower than the MIC of agent B when evaluated alone, antimicrobial agent B is able to effectively inhibit or prevent bacterial growth at concentrations lower than the MIC for agent B alone. Stated another way, when agents A and B are in combination, at least one of the agents is able to inhibit or prevent the growth of bacteria at a concentration lower than the concentration needed to inhibit or prevent growth of bacteria when only one of the agents of the combination is present.

Compositions for inhibiting the growth of bacteria formed in accordance with the present invention include antimicrobial agent A and antimicrobial agent B in amounts effective to inhibit the growth of bacteria, wherein agent A and agent B are selected from the group consisting of berberine, cedarwood oil, chloramphenicol, citral, citronella oil, cocamidopropyl dimethylglycine, *Glycyrrhiza glabra* extract, hinokitiol, juicy fruit basil oil, juniper berries oil, lemon basil oil, lemon oil, and *Rosmarinus officinalis* oil. An additional composition for inhibiting the growth of bacteria formed in accordance with the present invention includes geraniol and an antimicrobial agent selected from the group consisting of berberine, cedarwood oil, chloramphenicol, citronella oil, cocamidopropyl dimethylglycine, *Glycyrrhiza glabra* extract, hinokitiol, juicy fruit basil oil, juniper berries oil, lemon basil oil, lemon oil, and *Rosmarinus officinalis* oil.

In accordance with the present invention, the minimum inhibitory concentration of agent A in the presence of agent B is less than the minimum inhibitory concentration of agent A alone. In addition, preferably the minimum inhibitory concentration of agent B in the presence of agent A is less than the minimum inhibitory concentration of agent B alone. The compositions of the present invention are effective at inhibiting or preventing the growth of bacteria such as *Actinomyces viscosus, Campylobacter rectus, Fusobacterium nucleatum, Porphyromonas gingivalis, Streptococcus mutans*, and *Streptococcus sanguis*.

In addition, compositions formed in accordance with the present invention may include a third antimicrobial agent C different from antimicrobial agent A and antimicrobial agent B, and selected from berberine, cedarwood oil, chloramphenicol, citral, citronella oil, cocamidopropyl dimethylglycine, geraniol, *Glycyrrhiza glabra* extract, hinokitiol, juicy fruit basil oil, juniper berries oil, lemon basil oil, lemon oil, and *Rosmarinus officinalis* oil.

Compositions formed in accordance with the present invention are usefull in numerous products such as cleaners, wipes, pharmaceuticals and oral hygiene products. Examples of oral hygiene products include dentifrices and mouth rinses.

The compositions for inhibiting the growth of bacteria formed in accordance with the present invention can be used by contacting a surface with the composition.

BRIEF DESCRIPTION OF THE DRAWINGS

The FIGURE is a schematic illustration of the dilution scheme in a 96-well plate for a combination of three antimicrobial agents A, B, and C.

DETAILED DESCRIPTION OF THE PREFERRED EMBODIMENT

As used herein, the following terms have the following meanings.

"Berberine" refers to 5,6-dihydro-9,10-dimethoxybenzo [g]-1,3-benzodioxolo [5,6-a] quinolizinium and salts thereof. Berberine is an alkaloid isolated from *Hydrastis canadensis L.* and several other plants in the Berberidaceae family. Exemplary salts of berberine include berberine hydrochloride, berberine bisulfate, and berberine sulfate. The Chemical Abstract Service Registry (CAS) number for berberine is 84603-60-1.

"Cedarwood oil" refers to volatile whole oil extracts derived principally from the heartwood of *Juniperus virginiana* or *Juniperus ashei*. Constituents of the whole oil extract include thujopsene, cedrol, alpha-copaene, alpha-cedrene, beta-cedrene and widdrol. The CAS number for cedarwood oil is 8000-27-9.

"Chloramphenicol" refers to 2,2-dichloro-N-[2-hydroxyl-1-(hydroxymethyl)-2-(4-nitrophenyl)ethyl]acetamide. Chloramphenicol is derived from *Streptomyces venezuelae* or by organic synthesis. The CAS number for chloramphenicol is 56-75-7.

"Citral" refers to 3,7-dimethyl-2,6-octadienal. It is the volatile oil of *Cymbopogon citratus* and *Cymbopogon flexuosus* of the Gramineae family. Citral is available as a pure compound from commercial sources. The CAS number for citral is 5392-40-5.

"Citronella oil" refers to a commercially available oil produced by steam distillation of either *Cymbopogon nardus* or *Cymbopogon winterianus*. The CAS number for citronella oil is 8000-29-1.

"Geraniol" refers to trans-3,7-dimethyl-2,6-octadien-1-ol. The CAS number for geraniol is 106-24-1. Geraniol is found as a constituent in other essential oils such as citronella, lemon grass, rose oil, and palmarosa.

"N-cocamidopropyl-dimethylglycine" has a CAS number of 61789-40-0, 83138-0-3, and 86438-79-1.

"*Glycyrrhiza glabra* extract", also known as licorice root extract, refers to the crude powder extract from *Glycyrrhiza glabra*. Several varieties including *G. typica* and *G. glandulifera* exist. *Glycyrrhiza glabra* extract includes as constituents glycyrrhizic acid and glycyrrhetinic acid. The whole extract is available from commercial sources or may be collected by solvent extraction, such as the ethanol extraction described below.

"Hinokitiol" refers to beta-thujuplicin, which is an extract of *Thuja plicata*.

"Juicy fruit basil oil" refers to the whole extract of a selected variety of basil with a juicy fruit component. Juicy fruit basil is a cultivar of *Ocimum basilicur L.*

"Juniper berries oil" refers to volatile whole oil extract from the dried ripe fruit of *Juniperus communis*, Cupressaceae family. Juniper berries oil is also known as extract of Juniper, extract of *Juniperus communis*, and Juniper extract. The CAS number for Juniper berries oil is 84603-69-0.

"Lemon basil oil" refers to the volatile whole oil extract from a selected variety of basil with a citral component. Lemon basil is a cultivar of *Ocimum basilicum L* with a high content of citral.

"Lemon oil" refers to the volatile whole oil extract from the fresh peel of *Citrus limon*. Lemon oil is also known as oil of lemon or citrus limon oil. The CAS number for lemon oil is 8008-56-8.

"*Rosmarinus officinalis* oil" refers to the whole oil extract from the flowering tops of *Rosmarinus officinalis*. *Rosmarinus officinalis* oil is also known as the extract of Rosemary, or the extract of *Rosmarinus officinalis* oil. The CAS number for *Rosmarinus officinalis* oil is 84604-14-8.

Additional information regarding the essential oils described above can be found in Kirk-Othmer Encyclopedia of Chemical Technology, Fourth Edition, Volume 7, pages 603–674, John Wiley & Sons, Inc.

All of the foregoing are available from commercial sources.

"Minimal inhibitory concentration or MIC" refers to the minimum concentration in micrograms per milliliter of an antimicrobial agent at which no bacterial growth are observed. At concentrations below the MIC, the antimicrobial agent is ineffective at killing or inhibiting the growth and reproduction of bacteria. At concentrations above the MIC, the antimicrobial agent is effective at killing or inhibiting the growth and reproduction of bacteria.

It has been observed that combinations of antimicrobial agents formed in accordance with the present invention exhibit a surprising and unexpectedly significant decrease in the MIC of at least one, and preferably all of the antimicrobial agents in the combination compared to the MIC of a specific agent of the combination alone, i.e., in the absence of the other agents. This surprising reduction in MIC has been observed relative to representative gram-positive and gram-negative oral pathogenic bacteria such as *Actinomyces viscosus, Fusobacterium nucleatum, Porphyromonas gingivalis, Streptococcus mutans, Streptococcus sanguis* and *Campylobacter rectus*. For example, if the MIC for agent A alone is 10 and the MIC for agent B alone is 20, in accordance with the present invention, when agent A and agent B are combined, the MIC of agent A in the presence of agent B decreases relative to the MIC of agent A alone by an unexpected and surprising amount. Furthermore, preferably, the MIC of agent B in the presence of agent A decreases relative to the MIC of agent B alone by an amount that is surprising and unexpected. This reduction in the MIC of agent A and of agent B in the combination translates into the ability of agent A, and preferably agent B, to inhibit and/or prevent the growth and reproduction of bacteria at lower concentrations of antimicrobial agents A and B, compared to if only antimicrobial agent A or only antimicrobial agent B were present. As described in the background of the invention, typically the concentration of antimicrobial agents decreases from the time that the agents are initially applied. Thus, by effectively lowering the MIC of an antimicrobial agent, the period of time during which that antimicrobial agent can be expected to inhibit or prevent the growth of bacteria is extended. The surprising and unexpected results associated with the present invention will be described in more detail below and illustrated in the examples that follow.

Combinations of antimicrobial agents formed in accordance with the present invention include: (1) an antimicrobial agent A selected from berberine, cedarwood oil, chloramphenicol, citral, citronella oil, cocamidopropyl dimethylglycine, *Glycyrrhiza glabra* extract, hinokitiol, juicy fruit basil oil, Juniper berries oil, lemon basil oil, lemon oil, and *Rosmarinus officinalis* oil; and (2) an antimicrobial agent B different from antimicrobial agent A selected from the same list. In addition, combinations formed in accordance with the present invention include geraniol and an antimicrobial agent selected from berberine, cedarwood oil, chloramphenicol, citronella oil, cocamidopropyl dimethylglycine, *Glycyrrhiza glabra* extract, hinokitiol, juicy fruit basil oil, juniper berries oil, lemon basil oil, lemon oil, and *Rosmarinus officinalis* oil.

Of the many combinations of antimicrobial agents set forth above, preferred combinations include cedarwood oil and an antimicrobial agent selected from berberine, chloramphenicol, citral, cocamidopropyl dimethylglycine, geraniol, *Glycyrrhiza glabra* extract, hinokitiol, juicy fruit basil oil, and *Rosmarinus officinalis* oil. Most preferred are combinations of cedarwood oil with berberine, chloramphenicol, citral, cocamidopropyl dimethylglycine, geraniol, and *Glycyrrhiza glabra* extract.

Another preferred set of combinations includes berberine and an antimicrobial agent selected from chloramphenicol, citral, geraniol, *Glycyrrhiza glabra* extract, hinokitiol, juicy fruit basil oil, juniper berries oil, and lemon basil oil. Most preferred for combination with berberine are chloramphenicol, geraniol, *Glycyrrhiza glabra* extract, and lemon basil oil.

Other preferred combinations include hinokitiol in combination with chloramphenicol, citral, cocamidopropyl dimethylglycine, geraniol, *Glycyrrhiza glabra* extract, juniper berries oil, and lemon basil oil. Most preferred for combination with hinokitiol are antimicrobial agents selected from chloramphenicol, cocamidopropyl dimethylglycine, geraniol and *Glycyrrhiza glabra* extract.

Preferred results are obtained when *Glycyrrhiza glabra* extract is combined with antimicrobial agents selected from cedarwood oil, chloramphenicol, geraniol, juicy fruit basil oil, juniper berries oil, lemon basil oil, lemon oil, and *Rosmarinus officinalis* oil. Most preferred for combination with *Glycyrrhiza glabra* extract are antimicrobial agents selected from cedarwood oil, geraniol, juniper berries oil, *Rosmarinus officinalis* oil.

The foregoing combinations of the noted antibacterial agents are preferred and most preferred because of: (1) the degree to which the MIC of the individual antimicrobial agents in the combination is reduced compared to the MIC of those agents when evaluated alone; and (2) the MIC for the individual antimicrobial agents that is achieved due to the combination of agents.

In addition to compositions that include two antimicrobial agents as described above, the present invention also relates to compositions that include more than two, such as three or four antimicrobial agents wherein the MIC of at least one, and preferably all, of the constituent agents in the combination is reduced compared to the MIC of those constituents determined alone. Accordingly, an antimicrobial agent C selected from the groups set forth above wherein antimicrobial agent C is different from agent A and agent B and can be added to agent A and agent B to provide a three component composition in accordance with the present invention. Combinations of antimicrobial agents A, B and C formed in accordance with the present invention provide compositions wherein the MIC of at least one, and preferably all of the constituent agents, is reduced compared to the MIC of those constituents determined alone. In addition, in some instances, the MIC of the constituents in the combination of three antimicrobial agents is reduced relative to the MIC of various pairings of the three constituent agents.

The ratio of antimicrobial agents in compositions formed in accordance with the present invention is not limited to any particular values provided that the reduction in the MIC of the components of the combination is achieved as described above. Ratios for the two component compositions ranging from about 500:1 to about 1:500 have been observed to provide surprising and unexpected reductions in the MICs. In the three component system, any one agent can relate to the other two agents in a range from about 500:1 to about 1:500 to provide reductions in the MIC in accordance with the present invention.

The particular amount of antimicrobial agent present in compositions formed in accordance with the present invention is not limited to any particular value, provided that the amount present is effective at retarding the growth of bacteria and/or preventing the growth of bacteria, i.e. in an amount that is greater than the MIC of the antimicrobial agent with respect to the particular bacteria. When the compositions formed in accordance with the present invention are incorporated with various carriers, the amount of the antimicrobial agent present is preferably selected so that once the composition is applied or delivered, the concentration of the antimicrobial agent is greater than the MIC of the antimicrobial agent with respect to a particular bacteria. Suitable amounts range from about 0.001 wt. % to about 5.0 wt. %, preferably about 0.01 wt. % to about 2.5 wt. % for each agent based on the total weight of the composition containing the agents.

The compositions formed in accordance with the present invention are applied to surfaces where the inhibition of bacterial growth is desired. Examples of products used to control bacterial growth on surfaces include cleansers, wipes, pharmaceuticals, and preferably therapeutic products such as oral hygiene products, including dentifrices, mouth washes, and mouth rinses. Components of these products that are combined with the compositions of the present invention are preferably selected so that they do not have an antagonistic effect on the MIC lowering aspect of the compositions formed in accordance with the present invention.

Dentifrices, or toothpastes, are generally a thickened slurry of an abrasive polishing material in an aqueous humectant system. Typically, dentifrices include an abrasive to remove stained pellicle, humectant(s) to provide a vehicle for the flavor, abrasive, thickening agent(s) to structure and stabilize the dentifrice, surfactant mainly to supply foam during use, fluoride to prevent cavities, and flavor to make the product taste pleasant.

Numerous abrasives are available for use in dentifrices, examples include silica xerogel, silica precipitates, dicalcium phosphate, dicalcium phosphate dihydrate, alumina trihydrate, calcium pyrophosphate, calcium carbonate, and insoluble sodium metaphosphate.

Examples of suitable humectants include sorbitols, glycerin, and polyethylene glycols.

Silica aerogels, pyrogenic silica, silica precipitates, carboxymethylcellulose, carboxyvinyl polymers, xanthan gum, and carrageenan are examples of materials that are suitable as thickeners.

Exemplary surfactants include sodium lauryl sulfate and dodecylbenzene sulfonate.

Numerous flavoring agents are commercially available with those providing minty or other refreshing flavors such as cinnamon being commonly used.

Oral rinses or mouth washes are generally, aqueous, pourable emulsions of flavors into which, in most instances, an antimicrobial has been incorporated. Typical components of an oral rinse include flavoring agent to make the product pleasant to use and to emphasize therapeutic or freshness qualities, surfactant(s) to maintain flavor in stable dispersion, humectant(s) to improve mouth feel, thickening agent, and an active agent. Often times, a surfactant is used to impart light foaming properties to the oral rinse.

Dentifrices and oral rinses incorporating the compositions for inhibiting the growth of bacteria formed in accordance with the present invention are formulated in a conventional manner with the antimicrobial agents being present in an amount above their MICs as determined for the combination thereof.

The following examples illustrate the surprising and unexpected reduction in the MIC of the components when these components are combined in compositions for inhibiting the growth of bacteria formed in accordance with the present invention.

EXAMPLE 1

Determination of Minimum Inhibitory Concentration of Individual Agents and Two Antimicrobial Agents in Combination The following example illustrates how the MIC of individual antimicrobial agents that are combined to form a composition in accordance with the present invention were determined and also illustrates how the MIC of the antimicrobial agents in combination were determined.

A microtiter plate was used to dilute the antimicrobial agents to varying concentrations in order to determine the MIC of those antimicrobial agents alone and the MIC of the agents when combined to form a composition in accordance with the present invention.

A bacterial culture was incubated at 37° C. Prior to the dilution of the antimicrobial agents as described below, the bacterial culture was spun down at 2,000 rpm into a pellet and resuspended in a solution of buffered phosphate. The innoculum was normalized with a spectrophotometer to an optical density at 550 nanometers of between 0.180–0.220 (equivalent to $5.0 \times 10^7$ colony forming units, CFU per milliliter). The innoculum was set aside until the completion of the antimicrobial agent dilution.

A sterile polystyrene 96-well plate was used to dilute combinations of antimicrobial agent A and antimicrobial agent B. Using aseptic technique, 100 microliters of distilled water was placed in each test well. The dilution scheme of the antimicrobial agents was separated into two parts, the first part being the dilution of agent A and the second part being the dilution of agent B. One hundred microliters of stock solution for agent A was placed in the first well of each column. This was a one-half dilution based on the concentration of the stock solution. One hundred microliters was then transferred to the next well and so on down each of the test wells. Each transfer was a one-half dilution of the preceding well concentration. One hundred microliters of agent B stock solution was then added to the first well of each row and diluted across the plate in the same manner that agent A was diluted down the plate. After the dilution of agent B was completed, 80 microliters of growth media specific for the bacteria under study was added to each well.

In one column of the plate, 100 microliters of stock solution for agent A was placed in the first well. 100 microliters was then transferred to the next well and so on down each of the test wells in the column. Each transfer was a ½ dilution of the preceding well concentration of agent A. The foregoing was replicated in another column using agent B. These two columns were used to determine the MIC for agent A alone and agent B alone. After dilution of agent A alone and agent B alone was completed, 80 microliters of growth media specific for the bacteria under study was added to each well in these two columns.

Twenty microliters of innoculum was then added to each well. This resulted in the first well having a final dilution of one-quarter based on the concentration of the stock solutions. The remaining wells were a one-half dilution of the preceding well for each transfer. The 96-well plate was incubated under conditions that varied based on the particular microorganism. The aerobic bacteria *Actinomyces* viscosus, Streptococcus mutans and Streptococcus sanguis were incubated under ambient room conditions. The anaerobic bacteria Fusobacterium nucleatum and Porphyromonas gingivalis were incubated under an atmosphere of 10% hydrogen, 5% carbon dioxide and the balance nitrogen gas.

Following 48 hours of incubation, the incubated plate was read for microbial growth with a spectrophotometer by optical density (OD). The well containing the lowest dilution achievable for each agent with a spectrophotometer reading below 0.05 OD (i.e., no detectable microbial growth) was considered representative for the combination. The MIC for each agent in the combination was determined by accounting for the starting stock solution concentration and the resulting dilutions in the 96-well plate.

The specific bacteria inoculated into the 96-well plate are set forth in Table 1 below along with the growth media and the incubation conditions for that microorganism.

TABLE 1

Microorganisms/Growth Media/Incubation Conditions

| Microorganism | ATCC No. | Growth Media | Incubation Conditions |
|---|---|---|---|
| Actinomyces viscosus (AV) | 19246 | TSB[1] | 48 hrs/37° C./ aerobic |
| Fusobacterium nucleatum (FN) | 10933 | FN media[3] | 48 hrs/37° C./ anaerobic |
| Porphyromonas gingivalis (PG) | 33277 | PG media[2] | 48 hrs/37° C./ anaerobic |
| Streptococcus mutans (SM) | 25175 | TSB[1] | 48 hrs/37° C./ aerobic |
| Streptococcus sanguis (SS) | 49295 | TSB[1] | 48 hrs/37° C./ aerobic |

[1]Tryptic Soy Broth 3.0% wt. to vol., yeast extract 0.1%, and 999 milliliters distilled water.
[2]Tryptic Soy Broth 3.0% wt. to vol., yeast extract 0.5%, L-cystein 0.05%, Hemin 0.0005%, Menadione 0.00002%, and 990 milliliters distilled water.
[3]Tryptic Soy Broth 3.0% wt. to vol., yeast extract 0.5%, Peptone 1.0%, L-cystein extract, Hemin 0.0005%, Menadione 0.00002%, and 990 milliliters distilled water.

The antimicrobial agents from which agent A and agent B were selected are set forth in Table 2 below.

TABLE 2

Berberine hydrochloride (BX1)
Cedarwood oil (RC1)
Chloramphenicol (CR1)
Citral (CIT1)
Citronella oil (CTR1)
Cocamidopropyl dimethylglycine (TB1)
Geraniol (GRA1)
Glycyrrhiza glabra extract (GLY)
Hinokitiol (HK1)
Juicy fruit basil oil (JFB1)
Juniper berries oil (JPE1)
Lemon basil oil (LMB1)
Lemon oil (LMO1)
Rosmarinus officinalis oil (ROF1)

In the following tables, the respective antimicrobial agents A and B are identified with respect to the abbreviations set forth in Table 2. In addition, the five microorganisms set forth in Table 1 are referred to by the abbreviations set forth in Table 1.

Various combinations of the antimicrobial agents set forth in Table 2 were evaluated in accordance with the protocol set forth above in order to identify combinations of agents that will inhibit visible in vitro growth of microorganisms and evaluate the MIC of the agents in the combination. In addition, the lowest concentration, e.g., (MIC), of each of the antimicrobial agents used in the two component combinations that inhibited visible in vitro growth of a particular microorganism was determined in accordance with the protocol set forth above. The resulting data are summarized in Tables 3–16. In each of these tables, a mean MIC value is given for agent A alone. Because multiple well plates were inoculated and incubated in accordance with the procedure above in order to ascertain the information regarding the multiple combinations, in each run, a MIC for agent A alone was determined. The MIC for agent A alone given in Tables 3–16 represents the mean of these values.

TABLE 3

MIC of Cedarwood Oil Alone and in Combination with Antimicrobial Agent B

| Agent | | MIC ($\mu$g/ml) of Cedarwood Oil When Combined With Agent B for Identified Bacteria | | | | |
|---|---|---|---|---|---|---|
| A | B | AV | FN | PG | SM | SS |
| RCI | — | 36.5 | 36.5 | 7.8 | 31.3 | 15.6 |
| | +BX1 | 7.8 | 2.0 | 2.0 | 7.8 | 2.0 |
| | +CR1 | 7.8 | 3.9 | 2.0 | 2.0 | 7.8 |
| | +CIT1 | 7.8 | 7.8 | 3.9 | 7.8 | 2.0 |
| | +CTR1 | 2.0 | 15.6 | 3.9 | 7.8 | 7.8 |
| | +TB1 | 7.8 | 15.6 | 2.0 | 7.8 | 31.3 |
| | +GRA1 | 3.9 | 7.8 | 2.0 | 7.8 | 2.0 |
| | +GLY | 7.8 | 15.6 | 3.9 | 7.8 | 3.9 |
| | +HK1 | 15.6 | 15.6 | 3.9 | 7.8 | 7.8 |
| | +JFB1 | 7.8 | 15.6 | 3.9 | 2.0 | 3.9 |
| | +JPE1 | 2.0 | 15.6 | 3.9 | 7.8 | 7.8 |
| | +LMB1 | 2.0 | 2.0 | 3.9 | 7.8 | 3.9 |
| | +LMO1 | 7.8 | 15.6 | 3.9 | 7.8 | 3.9 |
| | +ROF1 | 15.6 | 15.6 | 3.9 | 3.9 | 7.8 |

TABLE 4

MIC of Berberine Hydrochloride Alone and in Combination With Antimicrobial Agent B

| Agent | | MIC ($\mu$g/ml) of Berberine Hydrochloride When Combined With Agent B for Identified Bacteria | | | | |
|---|---|---|---|---|---|---|
| A | B | AV | FN | PG | SM | SS |
| BX1 | — | 31.9 | 38.5 | 11.4 | 43.3 | 46.9 |
| | +RC1 | 3.9 | 15.6 | 7.8 | 3.9 | 7.8 |
| | +CR1 | 3.9 | 15.6 | 7.8 | 2.0 | 3.9 |
| | +CIT1 | 2.0 | 7.8 | 2.0 | 15.6 | 15.6 |
| | +CTR1 | 7.8 | 2.0 | 3.9 | 2.0 | 3.9 |
| | +TB1 | 31.3 | 31.3 | 7.8 | 31.3 | 15.6 |
| | +GRA1 | 3.9 | 7.8 | 2.0 | 7.8 | 15.6 |
| | +GLY | 15.6 | 15.6 | 7.8 | 15.6 | 15.6 |
| | +HK1 | 7.8 | 15.6 | 2.0 | 31.3 | 3.9 |
| | +JFB1 | 15.6 | 15.6 | 2.0 | 15.6 | 15.6 |
| | +JPE1 | 2.0 | 7.8 | 7.8 | 2.0 | 3.9 |
| | +LMB1 | 2.0 | 7.8 | 2.0 | 3.9 | 7.8 |
| | +LMO1 | 2.0 | 2.0 | 2.0 | 15.6 | 7.8 |
| | +ROF1 | 31.3 | 2.0 | 3.9 | 31.3 | 2.0 |

TABLE 5

MIC of Hinokitiol Alone and in Combination With Antimicrobial Agent B

| Agent | | MIC ($\mu$g/ml) of Hinokitiol When Combined With Agent B for Identified Bacteria | | | | |
|---|---|---|---|---|---|---|
| A | B | AV | FN | PG | SM | SS |
| HK1 | — | 0.8 | 2.1 | 2.1 | 0.8 | 0.9 |
| | +BX1 | 0.2 | 0.4 | 1.6 | 0.1 | 0.4 |

TABLE 5-continued

MIC of Hinokitiol Alone and in Combination With Antimicrobial Agent B

| Agent | | MIC (μg/ml) of Hinokitiol When Combined With Agent B for Identified Bacteria | | | | |
|---|---|---|---|---|---|---|
| A | B | AV | FN | PG | SM | SS |
| | +RC1 | 0.2 | 0.8 | 0.1 | 0.2 | 0.1 |
| | +CR1 | 0.2 | 0.8 | 0.4 | 0.2 | 0.2 |
| | +CIT1 | 0.4 | 0.8 | 0.8 | 0.4 | 0.4 |
| | +CTR1 | 0.1 | 0.1 | 0.8 | 0.1 | 0.4 |
| | +TB1 | 1.0 | 1.0 | 7.8 | 1.0 | 1.0 |
| | +GRA1 | 0.1 | 0.8 | 0.8 | 0.8 | 0.2 |
| | +GLY | 0.4 | 0.8 | 0.8 | 0.8 | 0.8 |
| | +JFB1 | 0.4 | 0.4 | 0.4 | 0.4 | 0.4 |
| | +JPE1 | 0.1 | 0.2 | 0.2 | 0.1 | 0.4 |
| | +LMB1 | 0.1 | 0.4 | 0.2 | 0.1 | 0.1 |
| | +LMO1 | 0.1 | 0.2 | 0.8 | 0.1 | 0.2 |
| | +ROF1 | 0.1 | 0.1 | 0.2 | 0.1 | 0.4 |

TABLE 6

MIC of *Glycyrrhiza glabra* Extract Alone and in Combination With Antimicrobial Agent B

| Agent | | MIC (μg/ml) of *Glycyrrhiza glabra* Extract When Combined With Agent B for Identified Bacteria | | | | |
|---|---|---|---|---|---|---|
| A | B | AV | FN | PG | SM | SS |
| GLY | — | 15.0 | 15.6 | 12.1 | 15.6 | 6.6 |
| | +BX1 | 7.8 | 3.9 | 1.0 | 7.8 | 3.9 |
| | +RC1 | 3.9 | 2.0 | 2.0 | 3.9 | 3.9 |
| | +CR1 | 1.0 | 1.0 | 1.0 | 3.9 | 2.0 |
| | +CIT1 | 1.0 | 1.0 | 2.0 | 1.0 | 1.0 |
| | +CTR1 | 3.9 | 2.0 | 3.9 | 3.9 | 1.0 |
| | +TB1 | 1.0 | 1.0 | 7.8 | 15.6 | 1.0 |
| | +GRA1 | 3.9 | 3.9 | 3.9 | 3.9 | 1.0 |
| | +HK1 | 7.8 | 3.9 | 1.0 | 1.0 | 1.0 |
| | +JFB1 | 1.0 | 2.0 | 2.0 | 1.0 | 2.0 |
| | +JPE1 | 3.9 | 2.0 | 3.9 | 1.0 | 1.0 |
| | +LMB1 | 3.9 | 3.9 | 2.0 | 3.9 | 1.0 |
| | +LMO1 | 2.0 | 2.0 | 2.0 | 3.9 | 1.0 |
| | +ROF1 | 1.0 | 2.0 | 1.0 | 1.0 | 2.0 |

TABLE 7

MIC of Geraniol Alone and in Combination With Antimicrobial Agent B

| Agent | | MIC (μg/ml) of Geraniol When Combined With Agent B for Identified Bacteria | | | | |
|---|---|---|---|---|---|---|
| A | B | AV | FN | PG | SM | SS |
| GRA1 | — | 133.3 | 82.3 | 147.9 | 133.3 | 127.1 |
| | +BX1 | 31.3 | 31.3 | 31.3 | 31.3 | 31.3 |
| | +RC1 | 62.5 | 15.6 | 15.6 | 31.3 | 31.3 |
| | +CR1 | 62.5 | 31.3 | 31.3 | 62.5 | 31.3 |
| | +CTR1 | 15.6 | 15.6 | 31.3 | 31.3 | 15.6 |
| | +TB1 | 12.5 | 31.3 | 31.3 | 125 | 62.5 |
| | +GLY | 62.5 | 15.6 | 3.9 | 62.5 | 31.3 |
| | +HK1 | 31.3 | 15.6 | 15.6 | 3.9 | 62.5 |
| | +JFB1 | 7.8 | 31.3 | 15.6 | 31.3 | 31.3 |
| | +JPE1 | 31.3 | 15.6 | 62.5 | 31.3 | 15.6 |
| | +LMB1 | 31.3 | 15.6 | 62.5 | 31.3 | 31.3 |
| | +LMO1 | 31.3 | 7.8 | 62.5 | 31.3 | 31.3 |
| | +ROF1 | 31.3 | 31.3 | 15.6 | 31.3 | 31.3 |

TABLE 8

MIC of Chloramphenicol Alone and in Combination With Antimicrobial Agent B

| Agent | | MIC (μg/ml) of Chloramphenicol When Combined With Agent B for Identified Bacteria | | | | |
|---|---|---|---|---|---|---|
| A | B | AV | FN | PG | SM | SS |
| CR1 | — | 5.4 | 1.8 | 6.9 | 5.2 | 3.2 |
| | +BX1 | 3.1 | 0.2 | 0.2 | 3.1 | 3.1 |
| | +RC1 | 0.4 | 1.6 | 0.8 | 3.1 | 0.8 |
| | +CIT1 | 0.2 | 0.2 | 0.2 | 0.2 | 0.4 |
| | +CTR1 | 1.6 | 0.4 | 3.1 | 1.6 | 1.6 |
| | +TB1 | 1.6 | 0.4 | 1.6 | 3.1 | 0.8 |
| | +GRA1 | 0.4 | 0.2 | 0.2 | 0.8 | 0.4 |
| | +GLY | 3.1 | 0.8 | 0.4 | 1.6 | 0.8 |
| | +HK1 | 3.1 | 0.8 | 0.4 | 3.1 | 3.1 |
| | +JFB1 | 0.2 | 0.4 | 1.6 | 3.1 | 0.4 |
| | +JPE1 | 1.6 | 0.2 | 1.6 | 0.2 | 0.2 |
| | +LMB1 | 1.6 | 0.4 | 0.4 | 3.1 | 0.2 |
| | +LMO1 | 1.6 | 0.2 | 0.2 | 1.6 | 0.8 |
| | +ROF1 | 0.2 | 0.2 | 3.1 | 0.2 | 0.2 |

TABLE 9

MIC of Citral Alone and in Combination With Antimicrobial Agent B

| Agent | | MIC (μg/ml) of Citral When Combined With Agent B for Identified Bacteria | | | | |
|---|---|---|---|---|---|---|
| A | B | AV | FN | PG | SM | SS |
| CIT1 | — | 212.5 | 76.1 | 75.0 | 171.1 | 147.9 |
| | +BX1 | 31.3 | 31.3 | 15.6 | 31.3 | 31.3 |
| | +RC1 | 125 | 125 | 62.5 | 125 | 125 |
| | +CR1 | 62.5 | 31.3 | 15.6 | 62.5 | 31.3 |
| | +CTR1 | 7.8 | 3.9 | 15.6 | 15.6 | 15.6 |
| | +TB1 | 125 | 31.3 | 31.3 | 62.5 | 31.3 |
| | +GLY | 125 | 31.3 | 15.6 | 125 | 7.8 |
| | +HK1 | 15.6 | 3.9 | 15.6 | 31.3 | 15.6 |
| | +JFB1 | 15.6 | 15.6 | 15.6 | 15.6 | 15.6 |
| | +JPE1 | 31.3 | 15.6 | 31.3 | 31.3 | 3.3 |
| | +LMB1 | 15.6 | 7.8 | 7.8 | 31.3 | 31.3 |
| | +LMO1 | 31.3 | 15.6 | 7.8 | 15.6 | 3.9 |
| | +ROF1 | 62.5 | 15.6 | 31.3 | 62.5 | 3.9 |

TABLE 10

MIC of Citronella Oil Alone and in Combination With Antimicrobial Agent B

| Agent | | MIC (μg/ml) of Citronella Oil When Combined With Agent B for Identified Bacteria | | | | |
|---|---|---|---|---|---|---|
| A | B | AV | FN | PG | SM | SS |
| CTR1 | — | 119.8 | 76.9 | 198.4 | 138.4 | 156.2 |
| | +BX1 | 31.3 | 31.3 | 7.8 | 62.5 | 31.3 |
| | +RC1 | 62.5 | 7.8 | 3.9 | 31.3 | 31.3 |
| | +CR1 | 31.3 | 15.6 | 15.6 | 31.3 | 3.9 |
| | +CIT1 | 62.5 | 15.6 | 15.6 | 62.5 | 62.5 |
| | +TB1 | 62.5 | 31.3 | 31.3 | 125 | 31.3 |
| | +GRA1 | 31.3 | 31.3 | 31.3 | 31.3 | 31.3 |
| | +GLY | 31.3 | 31.3 | 15.6 | 31.3 | 62.5 |
| | +HK1 | 62.5 | 31.3 | 3.9 | 62.5 | 7.8 |
| | +JFB1 | 31.3 | 15.6 | 31.3 | 31.3 | 31.3 |
| | +JPE1 | 31.3 | 7.8 | 31.3 | 31.3 | 31.3 |
| | +LMB1 | 3.9 | 15.6 | 31.3 | 7.8 | 7.8 |
| | +LMO1 | 3.9 | 15.6 | 31.3 | 15.6 | 15.6 |
| | +ROF1 | 31.3 | 15.6 | 15.6 | 31.3 | 7.8 |

TABLE 11

MIC of Juicy Fruit Basil Oil Alone and in Combination With Antimicrobial Agent B

| Agent | | MIC (μg/ml) of Juicy Fruit Basil Oil When Combined With Agent B for Identified Bacteria | | | | |
|---|---|---|---|---|---|---|
| A | B | AV | FN | PG | SM | SS |
| JFB1 | — | 89.6 | 73.7 | 36.9 | 95.8 | 93.8 |
| | +BX1 | 62.5 | 31.3 | 3.9 | 31.3 | 15.6 |
| | +RC1 | 62.5 | 31.3 | 3.9 | 62.5 | 31.3 |
| | +CR1 | 31.3 | 3.9 | 3.9 | 3.9 | 31.3 |
| | +CIT1 | 15.6 | 15.6 | 15.6 | 31.3 | 31.3 |
| | +CTR1 | 15.6 | 15.6 | 3.9 | 15.6 | 15.6 |
| | +TB1 | 31.3 | 31.3 | 15.6 | 62.5 | 62.5 |
| | +GRA1 | 31.3 | 15.6 | 15.6 | 15.6 | 31.3 |
| | +GLY | 62.5 | 31.3 | 15.6 | 62.5 | 31.3 |
| | +HK1 | 62.5 | 31.3 | 3.9 | 62.5 | 31.3 |
| | +JPE1 | 15.6 | 3.9 | 3.9 | 7.8 | 15.6 |
| | +LMB1 | 15.6 | 3.9 | 7.8 | 31.3 | 15.6 |
| | +LMO1 | 15.6 | 15.6 | 15.6 | 15.6 | 31.3 |
| | +ROF1 | 15.6 | 3.9 | 3.9 | 15.6 | 15.6 |

TABLE 12

MIC of Juniper Berries Oil Alone and in Combination With Antimicrobial Agent B

| Agent | | MIC (μg/ml) of Juniper Berries Oil When Combined With Agent B for Identified Bacteria | | | | |
|---|---|---|---|---|---|---|
| A | B | AV | FN | PG | SM | SS |
| JPE1 | — | 135.4 | 76.9 | 231.8 | 119.8 | 119.3 |
| | +BX1 | 31.3 | 31.3 | 7.8 | 62.5 | 31.3 |
| | +RC1 | 62.5 | 15.6 | 3.9 | 31.3 | 31.3 |
| | +CR1 | 31.3 | 7.8 | 15.6 | 62.5 | 31.3 |
| | +CIT1 | 62.5 | 15.6 | 7.8 | 62.5 | 31.3 |
| | +CTR1 | 31.3 | 15.6 | 31.3 | 31.3 | 31.3 |
| | +TB1 | 125 | 31.3 | 15.6 | 62.5 | 62.5 |
| | +GRA1 | 31.3 | 15.6 | 31.3 | 31.3 | 31.3 |
| | +GLY | 62.5 | 31.3 | 62.5 | 62.5 | 31.3 |
| | +HK1 | 62.5 | 31.3 | 7.8 | 62.5 | 15.6 |
| | +JFB1 | 31.3 | 15.6 | 62.5 | 31.3 | 31.3 |
| | +LMB1 | 31.3 | 15.6 | 62.5 | 31.3 | 31.3 |
| | +LMO1 | 31.3 | 15.6 | 62.5 | 15.6 | 31.3 |
| | +ROF1 | 62.5 | 15.6 | 31.3 | 31.3 | 15.6 |

TABLE 13

MIC of Lemon Basil Oil Alone and in Combination With Antimicrobial Agent B

| Agent | | MIC (μg/ml) of Lemon Basil Oil When Combined With Agent B for Identified Bacteria | | | | |
|---|---|---|---|---|---|---|
| A | B | AV | FN | PG | SM | SS |
| LMB1 | — | 125 | 81.7 | 200.5 | 130.2 | 132.8 |
| | +BX1 | 31.3 | 15.6 | 7.8 | 31.3 | 15.6 |
| | +RC1 | 62.5 | 31.3 | 3.9 | 15.6 | 31.3 |
| | +CR1 | 31.3 | 15.6 | 31.3 | 7.8 | 62.5 |
| | +CIT1 | 62.5 | 15.6 | 15.6 | 62.5 | 31.3 |
| | +CTR1 | 62.5 | 15.6 | 15.6 | 62.5 | 62.5 |
| | +TB1 | 62.5 | 15.6 | 15.6 | 62.5 | 31.3 |
| | +GRA1 | 15.6 | 15.6 | 31.3 | 31.3 | 15.6 |
| | +GLY | 31.3 | 15.6 | 31.3 | 62.5 | 15.6 |
| | +HK1 | 31.3 | 15.6 | 7.8 | 31.3 | 31.3 |
| | +JFB1 | 31.3 | 15.6 | 15.6 | 31.3 | 31.3 |
| | +JPE1 | 31.3 | 15.6 | 62.5 | 31.3 | 15.6 |
| | +LMO1 | 31.3 | 15.6 | 15.6 | 31.3 | 31.3 |
| | +ROF1 | 15.6 | 31.3 | 31.3 | 31.3 | 31.3 |

TABLE 14

MIC of Lemon Oil Alone and in Combination With Antimicrobial Agent B

| Agent | | MIC (μg/ml) of Lemon Oil When Combined With Agent B for Identified Bacteria | | | | |
|---|---|---|---|---|---|---|
| A | B | AV | FN | PG | SM | SS |
| LMO1 | — | 173.6 | 79.9 | 367.2 | 153.4 | 127.9 |
| | +BX1 | 62.5 | 31.3 | 15.6 | 62.5 | 31.3 |
| | +RC1 | 62.5 | 15.6 | 3.9 | 62.5 | 62.5 |
| | +CR1 | 31.3 | 15.6 | 15.6 | 31.3 | 31.3 |
| | +CIT1 | 62.5 | 15.6 | 31.3 | 62.5 | 62.5 |
| | +CTR1 | 62.5 | 15.6 | 15.6 | 62.5 | 62.5 |
| | +TB1 | 125 | 15.6 | 62.5 | 125 | 62.5 |
| | +GRA1 | 31.3 | 7.8 | 15.6 | 31.3 | 31.3 |
| | +GLY | 62.5 | 31.3 | 15.6 | 62.5 | 31.3 |
| | +HK1 | 125 | 31.3 | 7.8 | 125 | 62.5 |
| | +JFB1 | 15.6 | 15.6 | 31.3 | 31.3 | 31.3 |
| | +JPE1 | 31.3 | 15.6 | 31.3 | 31.3 | 31.3 |
| | +LMB1 | 31.3 | 15.6 | 15.6 | 31.3 | 31.3 |
| | +ROF1 | 31.3 | 31.3 | 31.3 | 31.3 | 31.3 |

TABLE 15

MIC of *Rosmarinus officinalis* Oil Alone and in Combination With Antimicrobial Agent B

| Agent | | MIC (μg/ml) of *Rosmarinus officinalis* Oil When Combined With Agent B for Identified Bacteria | | | | |
|---|---|---|---|---|---|---|
| A | B | AV | FN | PG | SM | SS |
| ROF1 | — | 192.3 | 72.1 | 184.9 | 174.1 | 132.8 |
| | +BX1 | 31.3 | 31.3 | 15.6 | 31.3 | 62.5 |
| | +RC1 | 7.8 | 15.6 | 7.8 | 62.5 | 31.3 |
| | +CR1 | 62.5 | 31.3 | 15.6 | 62.5 | 31.3 |
| | +CIT1 | 62.5 | 15.6 | 31.3 | 62.5 | 62.5 |
| | +CTR1 | 15.6 | 31.3 | 62.5 | 31.3 | 31.3 |
| | +TB1 | 125 | 31.3 | 62.5 | 125 | 31.3 |
| | +GRA1 | 31.3 | 15.6 | 31.3 | 31.3 | 31.3 |
| | +GLY | 125 | 31.3 | 15.6 | 125 | 7.8 |
| | +HK1 | 125 | 31.3 | 7.8 | 125 | 15.6 |
| | +JFB1 | 31.3 | 15.6 | 31.3 | 31.3 | 31.3 |
| | +JPE1 | 31.3 | 15.6 | 15.6 | 31.3 | 31.3 |
| | +LMB1 | 31.3 | 15.6 | 15.6 | 31.3 | 31.3 |
| | +LMO1 | 15.6 | 15.6 | 125 | 15.6 | 31.3 |

TABLE 16

MIC of Cocamidopropyl Dimethylglycine Alone and in Combination With Antimicrobial Agent B

| Agent | | MIC (μg/ml) of Cocamidopropyl Dimethylglycine When Combined With Agent B for Identified Bacteria | | | | |
|---|---|---|---|---|---|---|
| A | B | AV | FN | PG | SM | SS |
| TB1 | — | 28.9 | 45.4 | 16.8 | 22.8 | 30.2 |
| | +BX1 | 1.0 | 1.0 | 7.8 | 1.0 | 15.6 |
| | +RC1 | 1.0 | 7.8 | 2.0 | 1.0 | 0.1 |
| | +CR1 | 31.3 | 31.3 | 3.9 | 15.6 | 31.3 |
| | +CIT1 | 1.0 | 7.8 | 2.0 | 1.0 | 15.6 |
| | +CTR1 | 7.8 | 1.0 | 2.0 | 1.0 | 1.0 |
| | +GRA1 | 1.0 | 15.6 | 2.0 | 1.0 | 7.8 |
| | +GLY | 15.6 | 62.5 | 3.9 | 1.0 | 31.3 |
| | +HK1 | 1.0 | 1.0 | 7.8 | 1.0 | 1.0 |
| | +JFB1 | 7.8 | 1.0 | 1.0 | 3.9 | 1.0 |
| | +JPE1 | 1.0 | 1.0 | 2.0 | 1.0 | 1.0 |

TABLE 16-continued

MIC of Cocamidopropyl Dimethylglycine Alone and in Combination
With Antimicrobial Agent B

| Agent | | MIC (μg/ml) of Cocamidopropyl Dimethylglycine When Combined With Agent B for Identified Bacteria | | | | |
|---|---|---|---|---|---|---|
| A | B | AV | FN | PG | SM | SS |
|  | +LMB1 | 3.9 | 1.0 | 3.9 | 1.0 | 1.0 |
|  | +LMO1 | 1.0 | 3.9 | 3.9 | 1.0 | 1.0 |
|  | +ROF1 | 3.9 | 1.0 | 2.0 | 1.0 | 3.9 |

This example illustrates the effect that the addition of an antimicrobial agent B to antimicrobial agent A has on the MIC of antimicrobial agent A. The resulting data illustrate how the MIC of agent A when combined with agent B is reduced relative to the MIC of agent A alone.

EXAMPLE 2

Determination of MIC of Individual Apents and Three Antimicrobial Agents in Combination This example illustrates how combinations of three antimicrobial agents formed in accordance with the present invention inhibit visible in vitro growth of oral microorganisms. In addition, the example describes how the MIC of antimicrobial agents in the combinations are reduced compared to the MIC of those antimicrobial agents alone and the MIC of those agents in various pairings. Numerous combinations of the antimicrobial agents described herein were combined to form combinations comprising three antimicrobial agents or triplets. Each of the formed triplets included either cedarwood oil, berberine hydrochloride, or hinokitiol.

The protocol used was a variation of the procedure described above in Example 1. The assay was carried out in the two-dimensional array of a 96-well plate. In order to evaluate three agents, two of the agents were paired against the third agent. For example, varying concentrations of antimicrobial agent A plus antimicrobial agent B versus varying concentrations of antimicrobial agent C were evaluated on one 96-well plate. The procedure was repeated with the other two possible pairings, i.e., A+C with B, and B+C with A. Accordingly, each triplet required three assays in order to assess each of the three possible pairings.

The bacterial innoculum was prepared as described in Example 1.

A sterile polystyrene 96-well plate was used to dilute the antimicrobial agents A, B and C. Using aseptic technique, 100 microliters of distilled water was placed in each test well. The dilution scheme was separated into two parts. First, the dilution of the combined agents A and B and then second, the dilution of agent C. A dilution of agents A and B was accomplished by placing 50 microliters of stock solution for agent A in the first well of each column. Next, 50 microliters of stock solution for agent B was added to each of the first wells of each column. Accordingly, the first well of each column included 50 microliters of stock solution for agent A and 50 microliters of stock solution for agent B. 100 microliters from the first row in each column was then transferred to the next well in the column and so on down the column. Each transfer was a one-half dilution of the preceding concentration.

The dilution of antimicrobial agent C was accomplished by adding 100 microliters of agent C stock solution to the first well of each row. 100 microliters from the first well in each row was then transferred to the next well and so on across the row of test wells. Each transfer was a one-half dilution of the preceding concentration. The FIGURE is a schematic illustration of the concentrations of antimicrobial agents A, B and C derived from the dilution scheme described above. The stock solution for each antimicrobial agent had an initial concentration of 2,500 micrograms per milliliter. As illustrated in the FIGURE, the concentration of agents A and B decreases down a given column. The concentration of agent C decreases across a row from left to right. Upon completion of the dilution of agent C, at least one column remained which included diluted stock solution of A and B, with any agent C. This column of wells was used to assess the MIC for agent A and agent B in combination. In addition, stock solution of agent C was diluted down one column which provided an indication of the MIC for agent C alone. 80 microliters of growth media specific for the bacteria under study was added to each well. The growth media specific for the bacteria are set forth above in Table 1.

Next, 20 microliters of innoculum was added to each well. This resulted in the first well having a final dilution one-eighth of the stock solutions for agent A and agent B, and one-quarter dilution of the stock solution for agent C. The remaining wells were a half-dilution of the preceding well for each transfer.

The 96-well plate was then incubated under conditions that varied by microorganism. Table 1 lists the microorganisms and the specific incubation conditions. In addition to the bacteria set forth in Table 1, the bacteria *Campylobacter rectus* (CR) was utilized. The growth media for *Campylobacter rectus* was 0.74% wt. to vol. brain heart infusion broth, 0.01% yeast extract, 0.2% sodium formate, 0.03% sodium fumerate, and 0.005% hemin, and 990 milliliters distilled water. The incubation conditions for *Campylobacter rectus* were 48 hours at 37° C. under anaerobic conditions. The plate was then read for microbial growth with a spectrophotometer by optical density. The well containing the lowest dilution achievable for each agent with a spectrophotometer reading below 0.05 OD was considered representative for the combination. The MIC for each agent was then determined by accounting for the starting stock solution concentration and the resulting dilutions in the 96 well plate.

The resulting data are summarized in Tables 17–35.

TABLE 17

MIC of Cedarwood Oil, Citral and Geraniol Alone, in Pairs, and in Combination

| | | | MIC (μg/ml) for Identified Bacteria | | | | |
|---|---|---|---|---|---|---|---|
| A | B | C | AV | FN | PG | SM | SS |
| Individual Agents Alone[1] | | | | | | | |
| RC1 | — | — | 31.3 | 31.3 | 15.6 | 15.6 | 125 |
| — | CIT1 | — | 125 | 62.5 | 62.5 | 125 | 125 |
| — | — | GRA1 | 125 | 62.5 | 62.5 | 125 | 125 |
| Pairings of Agents A, B & C[2] | | | | | | | |
| RC1 | | | 15.6 | 15.6 | 7.8 | 15.6 | 31.3 |
| +CIT1 | | | 31.3 | 31.3 | 15.6 | 31.3 | 62.5 |
| RC1 | | | 15.6 | 15.6 | 7.8 | 15.6 | 31.3 |
| +GRA1 | | | 31.3 | 31.3 | 15.6 | 31.3 | 62.5 |
| CIT1 | | | 62.5 | 31.3 | 31.3 | 62.5 | 62.5 |
| +GRA1 | | | 62.5 | 31.3 | 31.3 | 62.5 | 62.5 |
| Triplets of Agents A, B & C[3] | | | | | | | |
| GRA1 | | | 7.8 | 31.3 | 15.6 | 3.9 | 31.3 |
|  | +RC1 | | 7.8 | 1 | 1 | 7.8 | 3.9 |
|  | +CIT1 | | 15.6 | 2 | 2 | 15.6 | 7.8 |
| CIT1 | | | 3.9 | 15.6 | 15.6 | 3.9 | 7.8 |

TABLE 17-continued

MIC of Cedarwood Oil, Citral and Geraniol Alone, in Pairs, and in Combination

| | | | MIC (μg/ml) for Identified Bacteria | | | | |
|---|---|---|---|---|---|---|---|
| A | B | C | AV | FN | PG | SM | SS |
| | +RC1 | | 7.8 | 3.9 | 1 | 7.8 | 7.8 |
| | +GRA1 | | 15.6 | 7.8 | 2 | 15.6 | 15.6 |
| RC1 | | | 7.8 | 15.6 | 3.9 | 7.8 | 7.8 |
| | +CIT | | 7.8 | 7.8 | 7.8 | 3.9 | 15.6 |
| | +GRA1 | | 7.8 | 7.8 | 7.8 | 3.9 | 15.6 |

[1]Directly to the right is shown the MIC values for each agent when used alone.
[2]Directly to the right is shown the MIC values for each agent in the presence of a second agent.
[3]Directly to the right is shown the MIC values for each agent in the presence of two additional agents.

TABLE 18

MIC of Cedarwood Oil Berberine Hydrochloride and Geraniol Alone, in Pairs, and in Combination

| | | | MIC (μg/ml) for Identified Bacteria | | | | |
|---|---|---|---|---|---|---|---|
| A | B | C | AV | FN | PG | SM | SS |
| Individual Agents Alone[1] | | | | | | | |
| RC1 | — | — | 31.3 | 62.5 | 15.6 | 31.3 | 7.8 |
| — | BX1 | — | 31.3 | 62.5 | 15.6 | 31.3 | 31.3 |
| — | — | GRA1 | 125 | 62.5 | 62.5 | 125 | 125 |
| Pairings of Agents A, B & C[2] | | | | | | | |
| RC1 | | | 15.6 | 15.6 | 7.8 | 15.6 | 3.9 |
| +BX1 | | | 15.6 | 15.6 | 7.8 | 15.6 | 3.9 |
| RC1 | | | 15.6 | 15.6 | 7.8 | 15.6 | 7.8 |
| +GRA1 | | | 31.3 | 31.3 | 15.6 | 31.3 | 15.6 |
| BX1 | | | 31.3 | 31.3 | 15.6 | 15.6 | 31.3 |
| +GRA1 | | | 62.5 | 31.3 | 31.3 | 31.3 | 62.5 |
| Triplets of Agents A, B & C[3] | | | | | | | |
| RC1 | | | 7.8 | 15.6 | 3.9 | 7.8 | 3.9 |
| | +BX1 | | 3.9 | 7.8 | 3.9 | 2.0 | 3.9 |
| | +GRA1 | | 7.8 | 7.8 | 7.8 | 3.9 | 7.8 |
| BX1 | | | 3.9 | 7.8 | 7.8 | 7.8 | 7.8 |
| | +RC1 | | 7.8 | 3.9 | 1.0 | 7.8 | 3.9 |
| | +GRA1 | | 15.6 | 7.8 | 2.0 | 15.6 | 7.8 |
| GRA1 | | | 7.8 | 15.6 | 15.6 | 31.3 | 31.3 |
| | +RC1 | | 7.8 | 3.9 | 1.0 | 7.8 | 1.0 |
| | +BX1 | | 7.8 | 3.9 | 1.0 | 7.8 | 1.0 |

TABLE 19

MIC of Red Cedarwood Oil, Berberine Hydrochloride and Hinokitiol Alone, in Pairs, and in Combination

| | | | MIC (μg/ml) for Identified Bacteria | | | | |
|---|---|---|---|---|---|---|---|
| A | B | C | AV | FN | PG | SM | SS |
| Individual Agents Alone[1] | | | | | | | |
| RC1 | — | — | 31.3 | 62.5 | 15.6 | 31.3 | 31.3 |
| — | BX1 | — | 31.3 | 62.5 | 15.6 | 31.3 | 31.3 |
| — | — | HK1 | 0.8 | 1.6 | 3.1 | 0.8 | 0.8 |
| Pairings of Agents A, B & C[2] | | | | | | | |
| RC1 | | | 15.6 | 15.6 | 7.8 | 15.6 | 3.9 |
| +BX1 | | | 15.6 | 15.6 | 7.8 | 15.6 | 3.9 |
| RC1 | | | 15.6 | 15.6 | 15.6 | 15.6 | 15.6 |
| +HK1 | | | 0.8 | 0.8 | 0.4 | 0.8 | 0.4 |
| BX1 | | | 15.6 | 15.6 | 15.6 | 15.6 | 15.6 |

TABLE 19-continued

MIC of Red Cedarwood Oil, Berberine Hydrochloride and Hinokitiol Alone, in Pairs, and in Combination

| | | | MIC (μg/ml) for Identified Bacteria | | | | |
|---|---|---|---|---|---|---|---|
| A | B | C | AV | FN | PG | SM | SS |
| +HK1 | | | 0.8 | 0.8 | 7.8 | 0.8 | 7.8 |
| Triplets of Agents A, B & C[3] | | | | | | | |
| RC1 | | | 15.6 | 7.8 | 3.9 | 7.8 | 3.9 |
| | +BX1 | | 1.0 | 3.9 | 3.9 | 3.9 | 3.9 |
| | +HK1 | | 0.05 | 0.2 | 2 | 0.2 | 2 |
| RC1 | | | 3.9 | 15.6 | 7.8 | 7.8 | 15.6 |
| | +RC1 | | 7.8 | 1.0 | 1.0 | 7.8 | 1.0 |
| | +HK1 | | 0.4 | 0.05 | 0.05 | 0.4 | 0.05 |
| HK1 | | | 0.2 | 0.4 | 0.8 | 0.2 | 0.4 |
| | +RC1 | | 7.8 | 3.9 | 3.9 | 7.8 | 1.0 |
| | +BX1 | | 7.8 | 3.9 | 3.9 | 7.8 | 1.0 |

TABLE 20

MIC of Red Cedarwood Oil, Berberine Hydrochloride and Juicy Fruit Basil Oil Alone, in Pairs, and in Combination

| | | | MIC (μg/ml) for Identified Bacteria | | | | |
|---|---|---|---|---|---|---|---|
| A | B | C | AV | FN | PG | SM | SS |
| Individual Agents Alone[1] | | | | | | | |
| RC1 | — | — | 15.6 | 31.3 | 62.5 | 15.6 | 15.6 |
| — | BX1 | — | 62.5 | 62.5 | 15.6 | 31.3 | 62.5 |
| — | — | JFB1 | 125 | 62.5 | 62.5 | 125 | 125 |
| Pairings of Agents A, B & C[2] | | | | | | | |
| RC1 | | | 15.6 | 15.6 | 7.8 | 15.6 | 7.8 |
| BX1 | | | 15.6 | 15.6 | 7.8 | 15.6 | 7.8 |
| RC1 | | | 7.8 | 2.0 | 1.0 | 7.8 | 1.0 |
| +JFB1 | | | 15.6 | 31.3 | 2.0 | 15.6 | 2.0 |
| BX1 | | | 31.3 | 15.6 | 7.8 | 15.6 | 15.6 |
| +JFB1 | | | 62.5 | 31.3 | 15.6 | 31.3 | 31.3 |
| Triplets of Agents A, B & C[3] | | | | | | | |
| RC1 | | | 7.8 | 7.8 | 7.8 | 7.8 | 7.8 |
| | BX1 | | 15.6 | 3.9 | 2.0 | 7.8 | 3.9 |
| | +JFB1 | | 31.3 | 7.8 | 3.9 | 15.6 | 7.8 |
| BX1 | | 15.6 | 15.6 | 3.9 | 7.8 | 31.3 | |
| | RC1 | | 7.8 | 7.8 | 2.0 | 1.0 | 7.8 1.0 |
| | +JFB1 | | 15.6 | 3.9 | 2.0 | 15.6 | 2.0 |
| JFB1 | | | 62.5 | 15.6 | 15.6 | 62.5 | 62.5 |
| | +RC1 | | 1.0 | 2.0 | 2.0 | 1.0 | 2.0 |
| | +BX1 | | 1.0 | 3.9 | 2.0 | 1.0 | 2.0 |

TABLE 21

MIC of Cedarwood Oil, Hinokitiol and Geraniol Alone, in Pairs, and in Combination

| | | | MIC (μg/ml) for Identified Bacteria | | | | |
|---|---|---|---|---|---|---|---|
| A | B | C | AV | FN | PG | SM | SS |
| Individual Agents Alone[1] | | | | | | | |
| RC1 | — | — | 7.8 | 62.5 | 7.8 | 15.6 | 15.6 |
| — | HK1 | — | 0.8 | 3.1 | 1.6 | 0.8 | 0.8 |
| — | — | GRA1 | 125 | 125 | 62.5 | 125 | 125 |
| Pairings of Agents A, B & C[2] | | | | | | | |
| RC1 | | | 15.6 | 15.6 | 15.6 | 15.6 | 7.8 |
| +HK1 | | | 0.8 | 0.8 | 0.8 | 0.8 | 0.4 |
| RC1 | | | 31.3 | 15.6 | 7.8 | 7.8 | 15.6 |
| +GRA1 | | | 62.5 | 31.3 | 15.6 | 15.6 | 31.3 |

TABLE 21-continued

MIC of Cedarwood Oil, Hinokitiol and Geraniol
Alone, in Pairs, and in Combination

| | | | MIC (μg/ml) for Identified Bacteria | | | | |
|---|---|---|---|---|---|---|---|
| A | B | C | AV | FN | PG | SM | SS |
| HK1 | | | 0.8 | 0.8 | 0.8 | 0.8 | 0.8 |
| +GRA1 | | | 31.3 | 31.3 | 31.3 | 31.3 | 31.3 |
| Triplets of Agents A, B & C[3] | | | | | | | |
| RC1 | | | 3.9 | 15.6 | 3.9 | 3.9 | 7.8 |
| | +HK1 | | 0.2 | 0.05 | 0.1 | 0.1 | 0.05 |
| | +GRA1 | | 7.8 | 2.0 | 3.9 | 3.9 | 2.0 |
| HK1 | | | 0.1 | 1.6 | 0.4 | 0.4 | 0.1 |
| | +RC1 | | 15.6 | 2.0 | 2.0 | 2.0 | 7.8 |
| | +GRA1 | | 31.3 | 3.9 | 3.9 | 3.9 | 15.6 |
| GRA1 | | | 15.6 | 31.3 | 62.5 | 7.8 | 62.5 |
| | +RC1 | | 7.8 | 2.0 | 3.9 | 7.8 | 1.0 |
| | +HK1 | | 0.4 | 0.1 | 0.2 | 0.4 | 0.5 |

TABLE 22

MIC of Cedarwood Oil, Hinokitiol and Citral
Alone, in Pairs, and in Combination

| | | | MIC (μg/ml) for Identified Bacteria | | | | |
|---|---|---|---|---|---|---|---|
| A | B | C | AV | FN | PG | SM | SS |
| Individual Agents Alone[1] | | | | | | | |
| RC1 | — | — | 7.8 | 62.5 | 15.6 | 15.6 | 15.6 |
| — | HK1 | — | 0.8 | 3.1 | 1.6 | 0.8 | 1.6 |
| — | — | CIT1 | 125 | 125 | 62.5 | 125 | 1.25 |
| Pairings of Agents A, B & C[2] | | | | | | | |
| RC1 | | | 15.6 | 15.6 | 7.8 | 15.6 | 7.8 |
| +HK1 | | | 0.8 | 0.8 | 0.4 | 0.8 | 0.8 |
| RC1 | | | 31.3 | 15.6 | 7.8 | 15.6 | 15.6 |
| +CIT1 | | | 62.5 | 31.3 | 15.6 | 31.3 | 31.3 |
| HK1 | | | 0.8 | 0.8 | 0.4 | 0.8 | 0.8 |
| +CIT1 | | | 31.3 | 31.3 | 15.6 | 31.3 | 31.3 |
| Triplets of Agents A, B & C[3] | | | | | | | |
| RC1 | | | 3.9 | 15.6 | 3.9 | 3.9 | 7.8 |
| | +HK1 | | 0.2 | 0.05 | 0.1 | 0.2 | 0.1 |
| | +CIT1 | | 7.8 | 2.0 | 3.9 | 7.8 | 3.9 |
| HK1 | | | 0.1 | 0.8 | 0.4 | 0.4 | 0.4 |
| | +RC1 | | 15.6 | 3.9 | 2.0 | 7.8 | 3.9 |
| | +CIT1 | | 31.3 | 7.8 | 3.9 | 15.6 | 7.8 |
| CIT1 | | | 7.8 | 31.3 | 3.9 | 7.8 | 62.5 |
| | +RC1 | | 7.8 | 2.0 | 3.9 | 7.8 | 1.0 |
| | +HK1 | | 0.4 | 0.1 | 0.2 | 0.4 | 0.1 |

TABLE 23

MIC of Cedarwood Oil, Hinokitiol and Juicy Fruit Basil Oil
Alone, in Pairs, and in Combination

| | | | MIC (μg/ml) for Identified Bacteria | | | | |
|---|---|---|---|---|---|---|---|
| A | B | C | AV | FN | PG | SM | SS |
| Individual Agents Alone[1] | | | | | | | |
| RC1 | — | — | 7.8 | 62.5 | 7.8 | 31.3 | 15.6 |
| — | HK1 | — | 0.8 | 3.1 | 3.1 | 0.8 | 0.8 |
| — | — | JFB1 | 125 | 125 | 15.6 | 62.5 | 125 |
| Pairings of Agents A, B & C[2] | | | | | | | |
| RC1 | | | 15.6 | 15.6 | 7.8 | 15.6 | 7.8 |
| +HK1 | | | 0.8 | 0.8 | 0.4 | 0.8 | 0.4 |
| RC1 | | | 31.3 | 15.6 | 3.9 | 15.6 | 15.6 |

TABLE 23-continued

MIC of Cedarwood Oil, Hinokitiol and Juicy Fruit Basil Oil
Alone, in Pairs, and in Combination

| | | | MIC (μg/ml) for Identified Bacteria | | | | |
|---|---|---|---|---|---|---|---|
| A | B | C | AV | FN | PG | SM | SS |
| +JFB1 | | | 62.5 | 31.3 | 7.8 | 31.3 | 31.3 |
| HK1 | | | 0.8 | 0.8 | 0.4 | 0.8 | 0.4 |
| +JFB1 | | | 31.3 | 31.3 | 15.6 | 31.3 | 15.6 |
| Triplets of Agents A, B & C[3] | | | | | | | |
| RC1 | | | 3.9 | 15.6 | 3.9 | 15.6 | 7.8 |
| | +HK1 | | 0.4 | 0.2 | 0.1 | 0.05 | 0.1 |
| | +JFB1 | | 15.6 | 7.8 | 3.9 | 2.0 | 3.9 |
| HK1 | | | 0.2 | 0.8 | 0.8 | 0.4 | 0.4 |
| | +RC1 | | 7.8 | 3.9 | 1.0 | 7.8 | 2.0 |
| | +JFB1 | | 15.6 | 7.8 | 2.0 | 15.6 | 3.9 |
| JFB1 | | | 62.5 | 31.3 | 7.8 | 15.6 | 31.3 |
| | +RC1 | | 3.9 | 3.9 | 1.0 | 7.8 | 2.0 |
| | +HK1 | | 0.2 | 0.2 | 0.05 | 0.4 | 0.1 |

TABLE 24

MIC of Cedarwood Oil, Berberine Hydrochloride and Citral
Alone, in Pairs, and in Combination

| | | | MIC (μg/ml) for Identified Bacteria | | | | |
|---|---|---|---|---|---|---|---|
| A | B | C | AV | FN | PG | SM | SS |
| Individual Agents Alone[1] | | | | | | | |
| RC1 | — | — | 15.6 | 62.5 | 7.8 | 15.6 | 15.6 |
| — | BX1 | — | 62.5 | 62.5 | 15.6 | 62.5 | 62.5 |
| — | — | CIT1 | 125 | 125 | 125 | 125 | 125 |
| Pairings of Agents A, B & C[2] | | | | | | | |
| RC1 | | | 15.6 | 31.3 | 3.9 | 7.8 | 15.6 |
| +BX1 | | | 15.6 | 31.3 | 3.9 | 7.8 | 15.6 |
| RC1 | | | 31.3 | 15.6 | 7.8 | 15.6 | 15.6 |
| +CIT1 | | | 62.5 | 31.3 | 15.6 | 31.3 | 31.3 |
| BX1 | | | 31.3 | 15.6 | 7.8 | 15.6 | 31.3 |
| +CIT1 | | | 62.5 | 31.3 | 15.6 | 31.3 | 62.5 |
| Triplets of Agents A, B & C[3] | | | | | | | |
| RC1 | | | 7.8 | 15.6 | 3.9 | 7.8 | 7.8 |
| | +BX1 | | 2.0 | 3.9 | 1.0 | 2.0 | 3.9 |
| | +CIT1 | | 3.9 | 7.8 | 2.0 | 3.9 | 7.8 |
| BX1 | | | 31.3 | 15.6 | 3.9 | 15.6 | 31.3 |
| | +RC1 | | 7.8 | 3.9 | 2.0 | 3.9 | 1.0 |
| | +CIT1 | | 15.6 | 7.8 | 3.9 | 7.8 | 2.0 |
| CIT1 | | | 62.5 | 62.5 | 31.3 | 62.5 | 31.3 |
| | +RC1 | | 3.9 | 3.9 | 1.0 | 1.0 | 3.9 |
| | BX1 | | 3.9 | 3.9 | 1.0 | 1.0 | 3.9 |

TABLE 25

MIC of Berberine Hydrochloride, Hinokitiol and Geraniol
Alone, in Pairs, and in Combination

| | | | MIC (μg/ml) for Identified Bacteria | | | | |
|---|---|---|---|---|---|---|---|
| A | B | C | AV | FN | PG | SM | SS |
| Individual Agents Alone[1] | | | | | | | |
| BX1 | — | — | 62.5 | 62.5 | 15.6 | 62.5 | 62.5 |
| — | HK1 | — | 0.8 | 3.1 | 1.6 | 0.8 | 0.8 |
| — | — | GRA1 | 125 | 125 | 125 | 125 | 250 |
| Pairings of Agents A, B & C[2] | | | | | | | |
| BX1 | | | 15.6 | 15.6 | 7.8 | 15.6 | 15.6 |
| +HK1 | | | 0.8 | 0.8 | 0.4 | 0.8 | 0.8 |

TABLE 25-continued

MIC of Berberine Hydrochloride, Hinokitiol and Geraniol
Alone, in Pairs, and in Combination

|   |   |   | MIC (µg/ml) for Identified Bacteria | | | | |
|---|---|---|---|---|---|---|---|
| A | B | C | AV | FN | PG | SM | SS |
| BX1 |   |   | 31.3 | 31.3 | 7.8 | 62.5 | 31.3 |
| +GRA1 |   |   | 62.5 | 62.5 | 15.6 | 62.5 | 62.5 |
| HK1 |   |   | 0.8 | 1.6 | 0.8 | 0.8 | 0.8 |
| +GRA1 |   |   | 31.3 | 62.5 | 31.3 | 31.3 | 31.3 |
| Triplets of Agents A, B & C[3] | | | | | | | |
| BX1 |   |   | 31.3 | 15.6 | 7.8 | 31.3 | 31.3 |
|   | +HK1 |   | 0.2 | 0.4 | 0.05 | 0.05 | 0.2 |
|   |   | +GRA1 | 7.8 | 15.6 | 2 | 2 | 7.8 |
| HK1 |   |   | 0.4 | 0.8 | 0.4 | 0.4 | 0.4 |
|   | +BX1 |   | 15.6 | 7.8 | 2 | 15.6 | 7.8 |
|   | +GRA1 |   | 31.3 | 15.6 | 3.9 | 31.3 | 15.6 |
| GRA1 |   |   | 62.5 | 31.3 | 31.3 | 62.5 | 31.3 |
|   | +BX1 |   | 7.8 | 2 | 1 | 7.8 | 3.9 |
|   | +HK1 |   | 0.4 | 0.1 | 0.05 | 0.4 | 0.2 |

TABLE 26

MIC of Berberine Hydrochloride, Hinokitiol and Juicy Fruit Basil Oil
Alone, in Pairs, and in Combination

|   |   |   | MIC (µg/ml) for Identified Bacteria | | | | |
|---|---|---|---|---|---|---|---|
| A | B | C | AV | FN | PG | SM | SS |
| Individual Agents Alone[1] | | | | | | | |
| BX1 | — | — | 62.5 | 62.5 | 15.6 | 62.5 | 62.5 |
| — | HK1 | — | 0.8 | 3.1 | 1.6 | 0.8 | 1.6 |
| — | — | JFB1 | 125 | 125 | 31.3 | 62.5 | 7.8 |
| Pairings of Agents A, B & C[2] | | | | | | | |
| BX1 |   |   | 15.6 | 31.3 | 15.6 | 15.6 | 15.6 |
| +HK1 |   |   | 0.8 | 1.6 | 0.8 | 0.8 | 0.8 |
| BX1 |   |   | 31.3 | 31.3 | 7.8 | 31.3 | 31.3 |
| +JFB1 |   |   | 62.5 | 62.5 | 15.6 | 62.5 | 62.5 |
| HK1 |   |   | 0.8 | 1.6 | 0.2 | 0.8 | 0.8 |
| +JFB1 |   |   | 31.3 | 62.5 | 7.8 | 31.3 | 31.3 |
| Triplets of Agents A, B & C[3] | | | | | | | |
| BX1 |   |   | 31.3 | 15.6 | 3.9 | 31.3 | 31.3 |
|   | +HK1 |   | 0.2 | 0.4 | 0.05 | 0.05 | 0.1 |
|   |   | +JFB1 | 7.8 | 15.6 | 2 | 2 | 3.9 |
| HK1 |   |   | 0.4 | 0.8 | 0.4 | 0.4 | 0.8 |
|   | +BX1 |   | 15.6 | 7.8 | 2 | 7.8 | 3.9 |
|   | +JFB1 |   | 31.3 | 15.6 | 3.9 | 15.6 | 7.8 |
| JFB1 |   |   | 62.5 | 31.3 | 7.8 | 15.6 | 3.9 |
|   | +BX1 |   | 1 | 7.8 | 3.9 | 7.8 | 2 |
|   | +HK1 |   | 1 | 0.4 | 0.2 | 0.4 | 0.1 |

TABLE 27

MIC of Berberine Hydrochloride, Hinokitiol and Citral
Alone, in Pairs, and in Combination

|   |   |   | MIC (µg/ml) for Identified Bacteria | | | | |
|---|---|---|---|---|---|---|---|
| A | B | C | AV | FN | PG | SM | SS |
| Individual Agents Alone[1] | | | | | | | |
| BX1 | — | — | 62.5 | 62.5 | 15.6 | 62.5 | 125 |
| — | HK1 | — | 0.8 | 3.1 | 1.6 | 0.8 | 0.8 |
| — | — | CIT1 | 125 | 125 | 31.3 | 250 | 125 |
| Pairings of Agents A, B & C[2] | | | | | | | |
| BX1 |   |   | 15.6 | 31.3 | 7.8 | 15.6 | 15.6 |

TABLE 27-continued

MIC of Berberine Hydrochloride, Hinokitiol and Citral
Alone, in Pairs, and in Combination

|   |   |   | MIC (µg/ml) for Identified Bacteria | | | | |
|---|---|---|---|---|---|---|---|
| A | B | C | AV | FN | PG | SM | SS |
| +HK1 |   |   | 0.8 | 1.6 | 0.2 | 0.8 | 0.8 |
| BX1 |   |   | 31.3 | 31.3 | 7.8 | 31.3 | 31.3 |
| +CIT1 |   |   | 62.5 | 62.5 | 15.6 | 62.5 | 62.5 |
| HK1 |   |   | 0.8 | 1.6 | 0.4 | 0.8 | 0.8 |
| +CIT1 |   |   | 31.3 | 62.5 | 15.6 | 31.3 | 31.3 |
| Triplets of Agents A, B & C[3] | | | | | | | |
| BX1 |   |   | 31.3 | 15.6 | 3.9 | 31.3 | 31.3 |
|   | +HK1 |   | 0.2 | 0.4 | 0.1 | 0.05 | 0.2 |
|   | +CIT1 |   | 7.8 | 15.6 | 3.9 | 2 | 7.8 |
| HK1 |   |   | 0.4 | 0.8 | 0.4 | 0.4 | 0.4 |
|   | +BX1 |   | 15.6 | 7.8 | 3.9 | 15.6 | 3.9 |
|   | +CIT1 |   | 31.3 | 15.6 | 7.8 | 31.3 | 7.8 |
| CIT1 |   |   | 62.5 | 31.3 | 7.8 | 125 | 62.5 |
|   | +BX1 |   | 3.9 | 7.8 | 2 | 1 | 1 |
|   | +HK1 |   | 0.2 | 0.4 | 0.05 | 0.05 | 0.05 |

TABLE 28

MIC of Hinokitiol, Geraniol and Citral
Alone, in Pairs, and in Combination

|   |   |   | MIC (µg/ml) for Identified Bacteria | | | | |
|---|---|---|---|---|---|---|---|
| A | B | C | AV | FN | PG | SM | SS |
| Individual Agents Alone[1] | | | | | | | |
| HK1 | — | — | 1.6 | 1.6 | 1.6 | 0.8 | 0.8 |
| — | GRA1 | — | 125 | 62.5 | 62.5 | 125 | 125 |
| — | — | CIT1 | 125 | 62.5 | 62.5 | 125 | 125 |
| Pairings of Agents A, B & C[2] | | | | | | | |
| HK1 |   |   | 0.8 | 0.8 | 1.6 | 0.8 | 0.8 |
| +GRA1 |   |   | 31.3 | 31.3 | 31.3 | 31.3 | 31.3 |
| HK1 |   |   | 0.8 | 0.8 | 1.6 | 0.8 | 0.8 |
| +CIT1 |   |   | 31.3 | 31.3 | 31.3 | 31.3 | 31.3 |
| GRA1 |   |   | 62.5 | 31.3 | 31.3 | 62.5 | 31.3 |
| +CIT1 |   |   | 62.5 | 31.3 | 31.3 | 62.5 | 31.3 |
| Triplets of Agents A, B & C[3] | | | | | | | |
| HK1 |   |   | 0.4 | 0.4 | 0.4 | 0.4 | 0.4 |
|   | +GRA1 |   | 15.6 | 15.6 | 7.8 | 31.3 | 15.6 |
|   | +CIT1 |   | 15.6 | 15.6 | 7.8 | 31.3 | 15.6 |
| GRA1 |   |   | 125 | 15.6 | 15.6 | 62.5 | 31.3 |
|   | +HK1 |   | 0.05 | 0.4 | 0.4 | 0.4 | 0.2 |
|   | +CIT1 |   | 2 | 15.6 | 7.8 | 15.6 | 7.8 |
| CIT1 |   |   | 62.5 | 7.8 | 15.6 | 62.5 | 7.8 |
|   | +HK1 |   | 0.4 | 0.4 | 0.4 | 0.4 | 0.4 |
|   | +GRA1 |   | 15.6 | 15.6 | 7.8 | 15.6 | 15.6 |

TABLE 29

MIC of Cedarwood Oil, Geraniol and Juicy Fruit Basil Oil
Alone, in Pairs, and in Combination

|   |   |   | MIC (µg/ml) for Identified Bacteria | | | | |
|---|---|---|---|---|---|---|---|
| A | B | C | AV | FN | PG | SM | SS |
| Individual Agents Alone[1] | | | | | | | |
| RC1 | — | — | 31.3 | 31.3 | 7.8 | 31.3 | 31.3 |
| — | GRA1 | — | 62.5 | 62.5 | 62.5 | 125 | 62.5 |
| — | — | JFB1 | 125 | 62.5 | 15.6 | 125 | 62.5 |

TABLE 29-continued

MIC of Cedarwood Oil, Geraniol and Juicy Fruit Basil Oil Alone, in Pairs, and in Combination

| | | | MIC (μg/ml) for Identified Bacteria | | | | |
|---|---|---|---|---|---|---|---|
| A | B | C | AV | FN | PG | SM | SS |

Pairings of Agents A, B & C[2]

| RC1 | | | 15.6 | 15.6 | 7.8 | 15.6 | 15.6 |
| +GRA1 | | | 31.3 | 31.3 | 15.6 | 31.3 | 31.3 |
| RC1 | | | 15.6 | 15.6 | 3.9 | 7.8 | 7.8 |
| +JFB1 | | | 31.3 | 31.3 | 7.8 | 15.6 | 15.6 |
| GRA1 | | | 31.3 | 31.3 | 15.6 | 62.5 | 31.3 |
| +JFB1 | | | 31.3 | 31.3 | 15.6 | 62.5 | 31.3 |

Triplets of Agents A, B & C[3]

| RC1 | | | 15.6 | 15.6 | 3.9 | 3.9 | 7.8 |
| | +GRA1 | | 2 | 2 | 3.9 | 31.3 | 7.8 |
| | +JFB1 | | 2 | 2 | 3.9 | 31.3 | 7.8 |
| GRA1 | | | 15.6 | 31.3 | 15.6 | 31.3 | 15.6 |
| | +RC1 | | 3.9 | 2 | 1 | 2 | 2 |
| | +JFB1 | | 7.8 | 3.9 | 2 | 3.9 | 3.9 |
| JFB1 | | | 62.5 | 15.6 | 7.8 | 62.5 | 15.6 |
| | +RC1 | | 1 | 3.9 | 1 | 3.9 | 3.9 |
| | +GRA1 | | 2 | 7.8 | 2 | 7.8 | 7.8 |

TABLE 30

MIC of Cedarwood Oil, Juicy Fruit Basil Oil and Citral Alone, in Pairs, and in Combination

| | | | MIC (μg/ml) for Identified Bacteria | | | | |
|---|---|---|---|---|---|---|---|
| A | B | C | AV | FN | PG | SM | SS |

Individual Agents Alone[1]

| RC1 | — | — | 31.3 | 31.3 | 7.8 | 31.3 | 31.3 |
| — | JFB1 | — | 125 | 62.5 | 250 | 125 | 62.5 |
| — | — | CIT1 | 125 | 62.5 | 250 | 125 | 62.5 |

Pairings of Agents A, B & C[2]

| RC1 | | | 31.3 | 15.6 | 7.8 | 15.6 | 7.8 |
| +JFB1 | | | 62.5 | 31.3 | 15.6 | 31.3 | 15.6 |
| RC1 | | | 15.6 | 15.6 | 62.5 | 15.6 | 15.6 |
| +CIT1 | | | 31.3 | 31.3 | 125 | 31.3 | 31.3 |
| JFB1 | | | 31.3 | 31.3 | 15.6 | 62.5 | 31.3 |
| +CIT1 | | | 31.3 | 31.3 | 15.6 | 62.5 | 31.3 |

Triplets of Agents A, B & C[3]

| RC1 | | | 15.6 | 3.9 | 2 | 3.9 | 7.8 |
| | +JFB1 | | 2 | 15.6 | 3.9 | 31.3 | 7.8 |
| | +CIT1 | | 2 | 15.6 | 3.9 | 31.3 | 7.8 |
| JFB1 | | | 62.5 | 7.8 | 7.8 | 62.5 | 3.9 |
| | +RC1 | | 1 | 7.8 | 31.3 | 2 | 7.8 |
| | +CIT1 | | 2 | 15.6 | 62.5 | 3.9 | 15.6 |
| CIT1 | | | 62.5 | 31.3 | 62.5 | 62.5 | 15.6 |
| | +RC1 | | 2 | 1 | 2 | 2 | 2 |
| | +JFB1 | | 3.9 | 2 | 3.9 | 3.9 | 3.9 |

TABLE 31

MIC of Berberine Hydrochloride, Juicy Fruit Basil Oil and Citral Alone, in Pairs, and in Combination

| | | | MIC (μg/ml) for Identified Bacteria | | | | |
|---|---|---|---|---|---|---|---|
| A | B | C | AV | FN | CR | SM | SS |

Individual Agents Alone[1]

| BX1 | — | — | 31.3 | 31.3 | 125 | 31.3 | 31.3 |
| — | JFB1 | — | 62.5 | 125 | 250 | 62.5 | 62.5 |

TABLE 31-continued

MIC of Berberine Hydrochloride, Juicy Fruit Basil Oil and Citral Alone, in Pairs, and in Combination

| | | | MIC (μg/ml) for Identified Bacteria | | | | |
|---|---|---|---|---|---|---|---|
| A | B | C | AV | FN | CR | SM | SS |

| — | — | CIT1 | 125 | 62.5 | 31.3 | 125 | 125 |

Pairings of Agents A, B & C[2]

| BX1 | | | 31.3 | 15.6 | 3.9 | 31.3 | 31.3 |
| +JFB1 | | | 62.5 | 31.3 | 7.8 | 62.5 | 62.5 |
| BX1 | | | 31.3 | 15.6 | 62.5 | 31.3 | 15.6 |
| +CIT1 | | | 62.5 | 31.3 | 125 | 62.5 | 31.3 |
| JFB1 | | | 31.3 | 31.3 | 125 | 31.3 | 31.3 |
| +CIT1 | | | 31.3 | 31.3 | 125 | 31.3 | 31.3 |

Triplets of Agents A, B & C[3]

| BX1 | | | 7.8 | 3.9 | 62.5 | 7.8 | 7.8 |
| | +JFB1 | | 15.6 | 15.6 | 3.9 | 15.6 | 7.8 |
| | +CIT1 | | 15.6 | 15.6 | 3.9 | 15.6 | 7.8 |
| JFB1 | | | 15.6 | 31.3 | 15.6 | 15.6 | 15.6 |
| | +BX1 | | 7.8 | 3.9 | 31.3 | 7.8 | 3.9 |
| | +CIT1 | | 15.6 | 7.8 | 62.5 | 15.6 | 7.8 |
| CIT1 | | | 15.6 | 31.3 | 7.8 | 15.6 | 31.3 |
| | +BX1 | | 15.6 | 1 | 1 | 15.6 | 7.8 |
| | +JFB1 | | 31.3 | 2 | 2 | 31.3 | 15.6 |

TABLE 32

MIC of Berberine Hydrochloride, Juicy Fruit Basil Oil and Geraniol Alone, in Pairs, and in Combination

| | | | MIC (μg/ml) for Identified Bacteria | | | | |
|---|---|---|---|---|---|---|---|
| A | B | C | AV | FN | CR | SM | SS |

Individual Agents Alone[1]

| BX1 | — | — | 62.5 | 62.5 | 125 | 62.5 | 62.5 |
| — | JFB1 | — | 125 | 125 | 250 | 125 | 125 |
| — | — | GRA1 | 125 | 125 | 250 | 125 | 250 |

Pairings of Agents A, B & C[2]

| BX1 | | | 31.3 | 15.6 | 62.5 | 31.3 | 31.3 |
| +JFB1 | | | 62.5 | 31.3 | 125 | 62.5 | 62.5 |
| BX1 | | | 31.3 | 15.6 | 62.5 | 31.3 | 31.3 |
| +GRA1 | | | 62.5 | 31.3 | 125 | 62.5 | 62.5 |
| JFB1 | | | 62.5 | 31.3 | 125 | 62.5 | 62.5 |
| +GRA1 | | | 62.5 | 31.3 | 125 | 62.5 | 62.5 |

Triplets of Agents A, B & C[3]

| BX1 | | | 15.6 | 15.6 | 62.5 | 15.6 | 15.6 |
| | +JFB1 | | 15.6 | 2 | 2 | 15.6 | 15.6 |
| | +GRA1 | | 15.6 | 2 | 2 | 15.6 | 15.6 |
| JFB1 | | | 31.3 | 31.3 | 31.3 | 31.3 | 31.3 |
| | +BX1 | | 7.8 | 2 | 31.3 | 7.8 | 7.8 |
| | +GRA1 | | 15.6 | 3.9 | 62.5 | 15.6 | 15.6 |
| GRA1 | | | 31.3 | 31.3 | 31.3 | 31.3 | 31.3 |
| | +BX1 | | 7.8 | 1 | 15.6 | 7.8 | 7.8 |
| | +JFB1 | | 15.6 | 2 | 31.3 | 15.6 | 15.6 |

TABLE 33

MIC of Berberine Hydrochloride, Citral and Geraniol Alone, in Pairs, and in Combination

| | | | MIC (μg/ml) for Identified Bacteria | | | | |
|---|---|---|---|---|---|---|---|
| A | B | C | AV | FN | CR | SM | SS |

Individual Agents Alone[1]

| BX1 | — | — | 62.5 | 62.5 | 125 | 62.5 | 62.5 |
| — | CIT1 | — | 125 | 125 | 250 | 125 | 125 |

TABLE 33-continued

MIC of Berberine Hydrochloride, Citral and Geraniol
Alone, in Pairs, and in Combination

| A | B | C | AV | FN | CR | SM | SS |
|---|---|---|---|---|---|---|---|
| — | — | GRA1 | 250 | 125 | 250 | 125 | 125 |
| Pairings of Agents A, B & C[2] | | | | | | | |
| BX1 | | | 31.3 | 31.3 | 62.5 | 31.3 | 15.6 |
| +CIT1 | | | 62.5 | 62.5 | 125 | 62.5 | 31.3 |
| BX1 | | | 31.3 | 15.6 | 62.5 | 15.6 | 15.6 |
| +GRA1 | | | 62.5 | 31.3 | 125 | 31.3 | 31.3 |
| CIT1 | | | 62.5 | 62.5 | 125 | 62.5 | 31.3 |
| +GRA1 | | | 62.5 | 62.5 | 125 | 62.5 | 31.3 |
| Triplets of Agents A, B & C[3] | | | | | | | |
| BX1 | | | 31.3 | 15.6 | 31.3 | 15.6 | 15.6 |
| | +CIT1 | | 15.6 | 7.8 | 31.3 | 15.6 | 7.8 |
| | +GRA1 | | 15.6 | 7.8 | 31.3 | 15.6 | 7.8 |
| CIT1 | | | 62.5 | 62.5 | 7.8 | 62.5 | 15.6 |
| | +BX1 | | 15.6 | 2 | 31.3 | 1 | 3.9 |
| | +GRA1 | | 31.3 | 3.9 | 62.5 | 2 | 7.8 |
| GRA1 | | | 62.5 | 31.3 | 62.5 | 62.5 | 31.3 |
| | +BX1 | | 7.8 | 2 | 7.8 | 7.8 | 1 |
| | +CIT1 | | 15.6 | 3.9 | 15.6 | 15.6 | 2 |

TABLE 34

MIC of Hinokitiol, Juicy Fruit Basil Oil and Citral
Alone, in Pairs, and in Combination

| A | B | C | AV | FN | CR | SM | SS |
|---|---|---|---|---|---|---|---|
| Individual Agents Alone[1] | | | | | | | |
| HK1 | — | — | 0.8 | 3.1 | 3.2 | 0.8 | 0.8 |
| — | JFB1 | — | 250 | 125 | 500 | 125 | 125 |
| — | — | CIT1 | 125 | 125 | 500 | 125 | 125 |
| Pairings of Agents A, B & C[2] | | | | | | | |
| HK1 | | | 0.8 | 1.6 | 3.2 | 0.8 | 0.8 |
| +JFB1 | | | 31.3 | 62.5 | 125 | 31.3 | 31.3 |
| HK1 | | | 0.8 | 0.8 | 3.2 | 0.8 | 0.8 |
| +CIT1 | | | 31.3 | 31.3 | 125 | 31.3 | 31.3 |
| JFB1 | | | 31.3 | 31.3 | 125 | 31.3 | 62.5 |
| +CIT1 | | | 31.3 | 31.3 | 125 | 31.3 | 62.5 |
| Triplets of Agents A, B & C[3] | | | | | | | |
| HK1 | | | 0.4 | 1.6 | 1.6 | 0.4 | 0.4 |
| | +JFB1 | | 15.6 | 2 | 15.6 | 15.6 | 15.6 |
| | +CIT1 | | 15.6 | 2 | 15.6 | 15.6 | 15.6 |
| JFB1 | | | 62.5 | 31.3 | 3.9 | 62.5 | 31.3 |
| | +HK1 | | 0.4 | 0.4 | 1.6 | 0.1 | 0.2 |
| | +CIT1 | | 7.8 | 15.6 | 62.5 | 3.9 | 7.8 |
| CIT1 | | | 31.3 | 31.3 | 7.8 | 62.5 | 31.3 |
| | +HK1 | | 0.2 | 0.4 | 1.6 | 0.05 | 0.2 |
| | +JFB1 | | 7.8 | 15.6 | 62.5 | 2 | 7.8 |

TABLE 35

MIC of Hinokitiol, Juicy Fruit Basil Oil and Geraniol
Alone, in Pairs, and in Combination

| A | B | C | AV | FN | CR | SM | SS |
|---|---|---|---|---|---|---|---|
| Individual Agents Alone[1] | | | | | | | |
| HK1 | — | — | 0.8 | 3.1 | 3.1 | 0.8 | 0.8 |
| — | JFB1 | — | 125 | 125 | 250 | 125 | 125 |
| — | — | GRA1 | 125 | 125 | 250 | 125 | 125 |
| Pairings of Agents A, B & C[2] | | | | | | | |
| HK1 | | | 0.8 | 1.6 | 3.1 | 0.8 | 0.8 |
| +JFB1 | | | 31.3 | 62.5 | 125 | 31.3 | 31.3 |
| HK1 | | | 0.8 | 1.6 | 0.8 | 1.6 | 0.8 |
| +GRA1 | | | 31.3 | 62.5 | 62.5 | 31.3 | 31.3 |
| JFB1 | | | 31.3 | 31.3 | 125 | 62.5 | 62.5 |
| +GRA1 | | | 31.3 | 31.3 | 125 | 62.5 | 62.5 |
| Triplets of Agents A, B & C[3] | | | | | | | |
| HK1 | | | 0.4 | 1.6 | 1.6 | 0.1 | 0.4 |
| | +JFB1 | | 7.8 | 7.8 | 3.9 | 31.3 | 15.6 |
| | +GRA1 | | 7.8 | 7.8 | 3.9 | 31.3 | 15.6 |
| JFB1 | | | 31.3 | 31.3 | 62.5 | 62.5 | 62.5 |
| | +HK1 | | 0.2 | 0.4 | 0.8 | 0.1 | 0.05 |
| | +GRA1 | | 7.8 | 15.6 | 31.3 | 3.9 | 2 |
| GRA1 | | | 62.5 | 31.3 | 62.5 | 62.5 | 62.5 |
| | +JFB1 | | 3.9 | 15.6 | 31.3 | 7.8 | 3.9 |
| | +HK1 | | 0.1 | 0.4 | 0.8 | 0.2 | 0.1 |

This example illustrates how the MIC of antimicrobial agents A, B and C in combination is reduced relative to the MIC of the individual antimicrobial agents in the absence of the other antimicrobial agents.

EXAMPLE 3

Dentifrice Formulations

The following example describes dentifrices comprising combinations of antimicrobial agents A, B, and C formed in accordance with the present invention.

TABLE 36

Formulation 18-12: 0.2% Cedarwood Oil, 0.1% Juicy Fruit Basil Oil, 0.02% Citral (W/W)

| Component | Wt. % |
|---|---|
| Sorbitol 70% in water | 39.72 |
| Poloxamer 407 (PLURONIC ® F127) | 5.0 |
| deionized water | 25.901 |
| Carbomer 940 (CARBOPOL ® 940) | 0.3 |
| sodium hydroxide | 0.205 |
| xanthan gum | 0.40 |
| glycerin | 2.5 |
| sodium fluoride | 0.254 |
| sodium saccharine | 0.400 |
| SYLODENT ® 750 (silica) | 10.0 |
| SYLODENT ® 15 (silica) | 12.0 |
| flavoring agent | 1.0 |
| titanium dioxide | 0.50 |
| sodium lauryl sulfate | 1.5 |
| cedarwood oil | 0.200 |
| juicy fruit basil oil | 0.100 |
| citral | 0.020 |

TABLE 37

Formulation 18-36: 0.4% Cedarwood Oil 0.01% Berberine Hydrochloride (W/W)

| Component | Wt. % |
| --- | --- |
| Sorbitol 70% in water | 40.050 |
| Poloxamer 407 (PLURONIC ® F127) | 5.0 |
| deionized water | 25.386 |
| Carbomer 940 (CARBOPOL ® 940) | 0.3 |
| sodium hydroxide | 0.2 |
| xanthan gum | 0.4 |
| glycerin | 5.0 |
| sodium fluoride | 0.254 |
| sodium saccharine | 0.800 |
| SYLODENT ® 750 (silica) | 10.0 |
| SYLODENT ® 15 (silica) | 10.0 |
| cedarwood oil | 0.40 |
| berberine hydrochloride hydrate | 0.01 |
| flavoring agent | 1.00 |
| FD&C Blue #1, 1% solution | 0.2 |
| sodium lauryl sulfate | 1.00 |

TABLE 38

Formulation 18-55: 0.4% Cedarwood Oil, 0.1%, Geraniol, and 0.01% Berberine Hydrochloride (W/W)

| Component | Wt. % |
| --- | --- |
| Sorbitol 70% | 40.05 |
| deionized water | 24.486 |
| berberine hydrochloride hydrate | 0.01 |
| Carbomer 940 (CARBOPOL ® 940) | 0.30 |
| Poloxamer 407 (PLURONIC ® F127) | 5.00 |
| sodium hydroxide | 0.20 |
| xanthan gum | 0.40 |
| sodium fluoride | 0.254 |
| sodium saccharine | 0.80 |
| SYLODENT ® 750 (silica) | 10.0 |
| SYLODENT ® 15 (silica) | 10.0 |
| flavoring agent | 1.0 |
| titanium dioxide | 1.0 |
| sodium lauryl sulfate | 1.0 |
| glycerin | 5.0 |
| cedarwood oil | 0.4 |
| geraniol | 0.10 |

TABLE 39

Formulation 18-37: 0.4% Cedarwood Oil, 0.1% Geraniol, and 0.05% Citral (W/W)

| Component | Wt. % |
| --- | --- |
| Sorbitol 70% in water | 40.050 |
| Poloxamer 407 (PLURONIC ® F127) | 5.0 |
| deionized water | 25.246 |
| Carbomer 940 (CARBOPOL ® 940) | 0.3 |
| sodium hydroxide | 0.2 |
| xanthan gum | 0.4 |
| glycerin | 5.0 |
| sodium fluoride | 0.254 |
| sodium saccharine | 0.800 |
| SYLODENT ® 750 (silica) | 10.0 |
| SYLODENT ® 15 (silica) | 10.0 |
| cedarwood oil | 0.40 |
| geraniol | 0.10 |
| citral | 0.050 |
| flavoring agent | 1.00 |
| FD&C Blue #1, 1% solution | 0.2 |
| sodium lauryl sulfate | 1.00 |

Carbomer refers to polymer composed of acrylic acid cross-linked with allyl sucrose available as CARBOPOL® 940. CARBOPOL® 940 is commercially available from B.F. Goodrich. SYLODENT® 750 is a silica gel (silicon dioxide) and SYLODENT® 15 is a silica gel (silicon dioxide). SYLODENT® is available commercially from W.R. Grace & Co.—Conn. Davison Chemical Division.

TABLE 40

Formulation 18-58: 0.4% Cedarwood Oil, 0.1% Geraniol (W/W)

| Component | Wt. % |
| --- | --- |
| Sorbitol 70% | 40.05 |
| deionized water | 25.286 |
| berberine hydrochloride hydrate | 0.01 |
| Carbomer 940 (CARBOPOL ® 940) | 0.3 |
| Poloxamer 407 (PLURONIC ® F127) | 5.0 |
| sodium hydroxide | 0.2 |
| xanthan gum | 0.4 |
| sodium fluoride | 0.254 |
| sodium saccharine | 0.8 |
| SYLODENT ® 750 (silica) | 10.0 |
| SYLODENT ® 15 (silica) | 10.0 |
| flavoring agent | 1.0 |
| FD&C Blue #1, 1% solution | 0.2 |
| sodium lauryl sulfate | 1.0 |
| glycerin | 5.0 |
| cedarwood oil | 0.4 |
| geraniol | 0.1 |

Poloxamer 407 is available under the trademark PLURONIC® F127 from BASF Corporation. PLURONIC® F127 is a nonionic difunctional block polymer terminating in primary hydroxyl groups with molecular weights ranging from 1,000 to about 15,000. They include polyoxyalkyline derivatives of propylene glycol.

The formulations described above were formed in a vacuum mixer by adding the deionized water and dispersing the Carbomer while pulling a vacuum. When the Carbomer was well dispersed, the sodium hydroxide was added. In another vessel, the 70% sorbitol solution and Poloxamer was heated and mixed. The Poloxamer solution was then added to the vacuum mixture and blended with the Carbomer mixture. Xanthan gum was then added to the glycerin, and the resulting solution was added to the vacuum mixer and incorporated into the mixture. The salts were then added to the vacuum mixer, followed by silicas which were slowly mixed in. Active agents, flavor, sodium lauryl sulfate and coloring agents were then added and allowed to mix until well incorporated.

EXAMPLE 4

Customer Acceptance

This example illustrates customer acceptance of dentifrice formulations incorporating combinations of antimicrobial agents A, B, and optionally C formed in accordance with the present invention.

The formulations set forth above in Tables 36–40 were evaluated for customer acceptance. Formulation 5–99 was a dentifrice available commercially as Listerine® Cool Mint gel.

The preference study was carried out with a group of approximately 20 people. One tube of dentifrice formulation was given to each person to use over the course of a week. At the end of the week, participants filled out a questionnaire, the results of which are summarized in Table 41 below. The scoring range was 1–10 with 1 being poor and 10 being good. The scores were tallied and averaged.

TABLE 41

Consumer Evaluation

| Formulation | 18-12 | 18-36 | 18-55 | 18-37 | 18-58 | 5-99 |
|---|---|---|---|---|---|---|
| Color | 6.61 | 6.52 | 3.20 | 7.13 | 7.17 | 7.25 |
| Appearance | 6.27 | 6.74 | 3.75 | 6.91 | 6.89 | 6.75 |
| Taste | 5.09 | 4.96 | 5.05 | 4.17 | 6.50 | 4.00 |
| After Taste | 5.22 | 5.13 | 5.20 | 4.48 | 6.50 | 3.85 |
| Aroma | 5.00 | 6.35 | 5.35 | 4.52 | 6.94 | 4.55 |
| Cleaning | 6.22 | 6.48 | 5.95 | 6.39 | 6.78 | 6.10 |
| Foam | 6.22 | 6.30 | 6.00 | 6.19 | 6.00 | 5.85 |
| Consistency | 6.09 | 6.39 | 6.25 | 6.04 | 5.67 | 5.75 |
| Dry Mouth | 6.09 | 6.26 | 7.05 | 6.78 | 7.94 | 5.70 |
| Next Morning Feel | 5.43 | 5.87 | 5.50 | 5.28 | 6.33 | 5.15 |
| Overall Mouth Feel | 5.61 | 5.78 | 5.80 | 5.57 | 6.61 | 4.45 |
| Overall Satisfaction | 5.04 | 5.37 | 5.20 | 5.53 | 6.44 | 4.20 |

This example illustrates that the overall consumer satisfaction for formulations with antimicrobial agents in accordance with the present invention is greater than the overall consumer satisfaction for the commercially available product, Listerine® Cool Mint gel.

EXAMPLE 5

Ethanol Extraction of *Glycyrrhiza glabra*

25 grams of powdered plant material from *Glycyrrhiza glabra* was combined with 250 grams of a 95:5 ethanol/water mixture. The mixture was stirred overnight at room temperature. Solids were removed from the stirred mixture with a No. 4 Whatman filter in a Buchner funnel. Further removal of solids was achieved with a No. 5 Whatman filter in a Buchner funnel. Additional solids were removed with a Whatman 1 micrometer filter in a Buchner funnel. A vacuum filtration apparatus and a 0.2 micrometer filter was employed to clean the solution a final time. The clean solution was then concentrated down to a solid using a rotovaporizer. Approximately, 2.5 grams of a rust colored solid was collected as the crude extract of *Glycyrrhiza glabra*.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An oral hygiene product comprising:
    antimicrobial agent A and antimicrobial agent B in an amount effective to inhibit the growth of oral pathogenic bacteria selected from the group consisting of *Actinomyces viscosus, Fusobacterium nucleatum, Porphyromonas gingivalis, Streptococcus mutans*, and *Streptococcus sanguis* wherein agents A and B are selected from the group consisting of berberine, cedarwood oil, chloramphenicol, citral, citronella oil, *Glycyrrhiza glabra* extract, juicy fruit basil oil, juniper berries oil, lemon basil oil, lemon oil, and *Rosmarinus officinalis* oil, wherein a minimum inhibitory concentration of agent A relative to at least one of the bacteria, in the presence of agent B, is synergistically less than the minimum inhibitory concentration of agent A alone.

2. The oral hygiene product of claim 1, wherein a minimum inhibitory concentration of agent B relative to at least one of the bacteria, in the presence of agent A, is synergistically less than the minimum inhibitory concentration of agent B alone.

3. The oral hygiene product of claim 1, wherein agent A is selected from the group consisting of cedarwood oil, berberine, and *Glycyrrhiza glabra* extract.

4. The oral hygiene product of claim 1, further comprising antimicrobial agent C, different from agent A and agent B, agent C being present in an amount effective to inhibit the growth of bacteria and selected from the group consisting of berberine, cedarwood oil, chloramphenicol, citral, citronella oil, *Glycyrrhiza glabra* extract, juicy fruit basil oil, juniper berries oil, lemon basil oil, lemon oil, and *Rosmarinus officinalis* oil.

5. The oral hygiene product of claim 1, wherein antimicrobial agent A is cedarwood oil and antimicrobial agent B is selected from the group consisting of berberine and *Glycyrrhiza glabra* extract.

6. The oral hygiene product of claim 1, wherein antimicrobial agent A is *Glycyrrhiza glabra* extract and antimicrobial agent B is selected from the group consisting of citronella oil, juicy fruit basil oil, juniper berries oil, and *Rosmarinus officinalis* oil.

7. The oral hygiene product of claim 1, wherein antimicrobial agent A is chloramphenicol and antimicrobial agent B is lemon oil.

8. The oral hygiene product of claim 1, wherein antimicrobial agent A is citral and antimicrobial agent B is selected from the group consisting of citronella oil, juicy fruit basil oil, juniper berries oil, lemon basil oil, lemon oil, and *Rosmarinus officinalis* oil.

9. The oral hygiene product of claim 1, wherein antimicrobial agent A is citronella oil and antimicrobial agent B is selected from the group consisting of juicy fruit basil oil, juniper berries oil, lemon oil, and *Rosmarinus officinalis* oil.

10. The oral hygiene product of claim 1, wherein antimicrobial agent A is juicy fruit basil oil and antimicrobial agent B is selected from the group consisting of juniper berries oil, lemon oil, and *Rosmarinus officinalis* oil.

11. The oral hygiene product of claim 1, wherein antimicrobial agent A is juniper berries oil and antimicrobial agent B is selected from the group consisting of lemon basil oil, lemon oil, and *Rosmarinus officinalis* oil.

12. The oral hygiene product of claim 1, wherein antimicrobial agent A is lemon basil oil and antimicrobial agent B is selected from the group consisting of lemon oil and *Rosmarinus officinalis* oil.

13. The oral hygiene product of claim 1, wherein antimicrobial agent A is lemon oil and antimicrobial agent B is *Rosmarinus officinalis* oil.

14. An oral hygiene product comprising:
    an antimicrobial agent A comprising geraniol; and
    an antimicrobial agent B selected from the group consisting of berberine, cedarwood oil, chloramphenicol, citronella oil, cocamidopropyl dimethylglycine, *Glycyrrhiza glabra* extract, juicy fruit basil oil, juniper berries oil, lemon basil oil, lemon oil, and *Rosmarinus officinalis* oil, antimicrobial agent A and antimicrobial agent B being present in an amount effective to inhibit the growth of oral pathogenic bacteria selected from the group consisting of *Actinomyces viscosus, Fusobacterium nucleatum, Poryhyromonas gingivalis, Streptococcus mutans*, and *Streptococcus sanguis*, wherein a minimum inhibitory concentration of agent A relative to at least one of the bacteria, in the presence of agent B, is synergistically less than the minimum inhibitory concentration of agent A alone.

15. The product of claim 14, further comprising an antimicrobial agent C different from antimicrobial agent A and antimicrobial agent B selected from the group consisting of berberine, cedarwood oil, chloramphenicol, citronella oil, *Glycyrrhiza glabra* extract, juicy fruit basil oil, juniper berries oil, lemon basil oil, lemon oil, and *Rosmarinus officinalis* oil.

16. The oral hygiene product of claim 14, wherein antimicrobial agent B is selected from the group consisting of juniper berries oil, lemon basil oil, lemon oil, *Rosmarinus officinalis* oil, and cedarwood oil.

17. An oral hygiene product comprising:

an antimicrobial agent A comprising cocamidopropyl dimethylglycine; and an antimicrobial agent B selected from the group consisting of berberine, cedarwood oil, chloramphenicol, citral, citronella oil, *Glycyrrhiza glabra* extract, juicy fruit basil oil, juniper berries oil, lemon basil oil, lemon oil, and *Rosmarinus officinalis* oil, antimicrobial agent A and antimicrobial agent B being present in an amount effective to inhibit the growth of oral pathogenic bacteria selected from the group consisting of *Actinomyces viscosus, Fusobacterium nucleatum, Porphyromonas gingivalis, Streptococcus mutans*, and *Streptococcus sanguis*, wherein a minimum inhibitory concentration of agent A relative to at least one of the bacteria, in the presence of agent B, is synergistically less than the minimum inhibitory concentration of agent A alone.

18. A method for inhibiting the growth of bacteria within an oral cavity comprising the step:

contacting the oral cavity with a composition that includes antimicrobial agent A and antimicrobial agent B in an amount effective to inhibit the growth of oral pathogenic bacteria selected from the group consisting of *Actinomyces viscosus, Fusobacterium nucleatum, Porphyromonas gingivalis, Streptococcus mutans*, and *Streptococcus sanguis*, agents A and B selected from the group consisting of berberine, cedarwood oil, chloramphenicol, citral, citronella oil, *Glycyrrhiza glabra* extract, juicy fruit basil oil, juniper berries oil, lemon basil oil, lemon oil, and *Rosmarinus officinalis* oil, wherein the minimum inhibitory concentration of agent A relative to at least one of the bacteria, in the presence of agent B, is synergistically less than the minimum inhibitory concentration of agent A alone.

19. The method of claim 18, wherein the minimum inhibitory concentration of agent B relative to at least one of the bacteria, in the presence of agent A, is synergistically less than the minimum inhibitory concentration of agent B alone.

20. The method of claim 18, wherein the antimicrobial agent A is selected from the group consisting of cedarwood oil, berberine, and *Glycyrrhiza glabra* extract.

21. The method of claim 18, wherein the composition that includes antimicrobial agents A and B further comprises an antimicrobial agent C different from agent A and agent B, agent C selected from the group consisting of berberine, cedarwood oil, chloramphenicol, citral, citronella oil, *Glycyrrhiza glabra* extract, juicy fruit basil oil, juniper berries oil, lemon basil oil, lemon oil, and *Rosmarinus officinalis* oil.

22. A method of inhibiting the growth of oral pathogenic bacteria selected from the group consisting of *Actinomyces viscosus, Fusobacterium nucleatum, Porphyromonas gingivalis, Streptococcus mutans*, and *Streptococcus sanguis* within an oral cavity comprising the steps of contacting the oral cavity with the product of claim 14.

23. A method of reducing the minimum inhibitory concentration relative to oral pathogenic bacteria selected the group consisting of *Actinomyces viscosus, Fusobacterium nucleatum, Poryhyromonas gingivalis, Streptococcus mutans*, and *Streptococcus sanguis*, of an antimicrobial agent A selected from the group consisting of berberine, cedarwood oil, chloramphenicol, citral, citronella oil, geraniol, *Glycyrrhiza glabra* extract, juicy fruit basil oil, juniper berries oil, lemon basil oil, lemon oil, and *Rosmarinus officinalis* oil, comprising:

combining agent A with an antimicrobial agent B different from agent A, agent B being present in an amount effective to provide a synergistic reduction in the minimum inhibitory concentration of agent A relative to at least one of the bacteria, agent B selected from the group consisting of berberine, cedarwood oil, chloramphenicol, citral, citronella oil, geraniol, *Glycyrrhiza glabra* extract, juicy fruit basil oil, juniper berries oil, lemon basil oil, lemon oil, and *Rosmarinus officinalis* oil.

24. A method for reducing the minimum inhibitory concentration of an antimicrobial agent A comprising cocamidopropyl dimethylglycine comprising:

combining agent A with an antimicrobial agent B different than agent A, agent B being present in an amount effective to provide a synergistic reduction in the minimum inhibitory concentration of agent A relative to at least one of the bacteria, agent B selected from the group consisting of berberine, cedarwood oil, chloramphenicol, citral, citronella oil, geraniol, *Glycyrrhiza glabra* extract, juicy fruit basil oil, juniper berries oil, lemon basil oil, lemon oil, and *Rosmarinus officinalis* oil.

* * * * *

UNITED STATES PATENT AND TRADEMARK OFFICE
CERTIFICATE OF CORRECTION

PATENT NO. : 5,939,050
DATED : August 17, 1999
INVENTOR(S) : L.M. Iyer et al.

Page 1 of 2

It is certified that error appears in the above-identified patent and that said Letters Patent is hereby corrected as shown below:

| COLUMN | LINE | |
|---|---|---|
| [56] Pg. 1, col. 2 | Refs. Cited (Other Refs., Item 9) | "Yokata" should read --Yokota-- |
| [56] Pg. 1, col. 2 | Refs. Cited (Other Refs., Item 9) | "cheifly against Staphyloccus" should read --chiefly against Staphylococcus-- |
| [56] Pg. 1, col. 2 | Refs. Cited (Other Refs., Item 10) | "cheifly" should read --chiefly-- |
| [56] Pg. 1, col. 2 | Refs. Cited (Other Refs., Item 10) | after "Seibutsugaku;" insert a space |
| [56] Pg. 1, col. 2 | Refs. Cited (Other Refs., Item 11) | after "*Polonica*" insert a space |
| [56] Pg. 1, col. 2 | Refs. Cited (Other Refs., Item 12) | after "Translation of" insert a space |
| [56] Pg. 1, col. 2 | Refs. Cited (Other Refs., Item 15) | before "1994." insert --*ASSN:0019-1604*; Igaku to Seibutsugaku; 128(3):105-10; -- |

UNITED STATES PATENT AND TRADEMARK OFFICE
CERTIFICATE OF CORRECTION

PATENT NO. : 5,939,050  
DATED : August 17, 1999  
INVENTOR(S) : L.M. Iyer et al.

Page 2 of 2

It is certified that error appears in the above-identified patent and that said Letters Patent is hereby corrected as shown below:

| COLUMN | LINE | |
|---|---|---|
| [56]<br>Pg. 1, col. 2 | Refs. Cited<br>(Other Refs.,<br>after last<br>entry) | after the last Other Reference, please insert<br>--Kabara, J.J., "Medium-Chain Fatty Acids and Esters as Antimicrobial Agents," *Cosmetic and Drug Preservation: Principles and Practice*, pp. 274-304, 1984.<br>Mookherjec, B.D. et al., "Oils, Essential," *Encyclopedia of Chemical Technology*, 4th Ed., v. 17, pp. 603-674, 1996.-- |
| 32<br>(Claim 23 | 19<br>line 4) | "Poryhyromonas" should read<br>--Porphyromonas-- |

Signed and Sealed this

Thirtieth Day of May, 2000

Attest:

Q. TODD DICKINSON

*Attesting Officer*  
*Director of Patents and Trademarks*